US008796179B2

(12) United States Patent
Levenfors et al.

(10) Patent No.: US 8,796,179 B2
(45) Date of Patent: Aug. 5, 2014

(54) **FLUORESCENT PSEUDOMONAD OF THE SPECIES *PSEUDOMONAS AZOTOFORMANS* FOR ENHANCEMENT OF PLANT EMERGENCE AND GROWTH**

(75) Inventors: Jolanta Levenfors, Örbyhus (SE); Christopher Folkeson Welch, Uppsala (SE); Jamshid Fatehi, Skyttorp (SE); Mariann Wikstrom, Åstorp (SE); Sara Rasmussen, Landskrona (SE); Margareta Hökeberg, Uppsala (SE)

(73) Assignee: Lantmannen Bioagri AB, Uppsala (SE)

( * ) Notice: Subject to any disclaimer, the term of this patent is extended or adjusted under 35 U.S.C. 154(b) by 0 days.

(21) Appl. No.: 13/514,929

(22) PCT Filed: Dec. 22, 2010

(86) PCT No.: PCT/SE2010/051468
§ 371 (c)(1),
(2), (4) Date: Aug. 28, 2012

(87) PCT Pub. No.: WO2011/078783
PCT Pub. Date: Jun. 30, 2011

(65) Prior Publication Data
US 2013/0005572 A1 Jan. 3, 2013

Related U.S. Application Data

(60) Provisional application No. 61/289,058, filed on Dec. 22, 2009.

(51) Int. Cl.
*A01N 25/00* (2006.01)
*C12N 1/20* (2006.01)

(52) U.S. Cl.
USPC ..................................... 504/116.1; 435/253.3

(58) Field of Classification Search
None
See application file for complete search history.

(56) References Cited

U.S. PATENT DOCUMENTS

| 4,849,008 | A | * | 7/1989 | Schroth et al. ................. 504/117 |
| 5,503,651 | A |  | 4/1996 | Kloepper et al. |
| 5,503,652 | A |  | 4/1996 | Kloepper et al. |
| 5,935,839 | A |  | 8/1999 | Kloepper |
| 6,048,713 | A | * | 4/2000 | Murakami et al. ............ 435/91.2 |
| 6,447,770 | B1 |  | 9/2002 | Raaijmakers et al. |
| 6,495,362 | B1 |  | 12/2002 | Nautiyal |
| 2003/0054959 | A1 | * | 3/2003 | Boyetchko et al. ........... 504/117 |
| 2006/0178269 | A1 |  | 8/2006 | Medina-Vega |

FOREIGN PATENT DOCUMENTS

| CA | 2377054 | 9/2002 |
| CN | 1772881 | 5/2006 |
| CN | 101575583 | 11/2009 |
| CN | 101899409 | 12/2010 |
| CN | 102002468 | 4/2011 |
| JP | 2003250558 | 9/2003 |
| WO | WO 87/00194 | 1/1987 |
| WO | WO 00/51435 | 9/2000 |
| WO | WO 03/016241 | 2/2003 |
| WO | WO-03016241 | * 2/2003 |
| WO | WO 2007/056848 | 5/2007 |

OTHER PUBLICATIONS

Benizri et al., "Root Colonization by Inoculated Plant Growth-Promoting Rhizobacteria," *Biocontrol Science and Technology* 11: 557-574, 2001.
Brisbane et al., "Inhibition of fungi from wheat roots by *Pseudomonas fluorescens* 2-79 and fungicides," *Soil Biol. Biochem.*, 21(8): 1019-1025, 1989.
Compant et al., "Use of Plant Growth-Promoting Principles, Mechanisms of Action, 71(9): 4951-4959, Sep. 2005 Bacteria for Biocontrol of Plant Diseases: and Future Prospects," *Appl. and Environ. Microbiol.*, 71(9):4951-5959, Sep. 2005.
Dabboussi et al., "*Pseudomonas libanensis* sp. nov., a new species isolated from Lebanese spring waters," Int J Syst Bacteriol., 49 Pt 3: 1091-1101, Jul. 1999.
Davies and Whitbread, "Factors affecting the colonisation of a root system by fluorescent *Pseudomonads*: The effects of water, temperature and soil microflora," *Plant and Soil*, 116: 247-256, 1989.
DeFreitas and Germida,"*Pseudomonas cepacia* and *Pseudomonas putida* as winter wheat inoculants for biocontrol of *Rhizoctonia solani,*" *Can. J. Microbiol.*, 37(10): 780-784, 1991.
Deshwal et al., "Long-term effect of *Pseudomonas aeruginosa* GRC1 on yield of subsequent crops of paddy after mustard seed bacterization," *Current Science*, 91(4): 423-424, Aug. 2006.
Dowling and Gara, "Metabolites of *Pseudomonas* involved in the biocontrol of plant disease," *Trends Biotechnol.* 12: 133-141, Apr. 1994.
Franzetti et al., "*Pseudomonas* infections in patients with AIDS and AIDS-related complex," *J Intern Med.* 231(4):437-443, Apr. 1992.
García de Salamone et al., "Cytokinin production by plant growth promoting rhizobacteria and selected mutants," *Can. J. Microbiol.*, 47(5): 404-411, 2001.
Gerhardson and Ramert, "Plant reactions to inoculation of roots with fungi and bacteria," *J. Phytopathol.* 114(2): 108-117, Oct. 1985.
Hemming, "Bacteria as antagonists in biological control of plant pathogens," In: Baker and Dunn, *New directions in biological control: Alternatives for suppressing agricultural pests and diseases.* New York: Alan R. Liss. 223-242, 1990.
Hökeberg et al., "Biological control of cereal seed-borne diseases by seed bacterization with greenhouse selected bacteria," *European Journal of Plant Pathology*, 103(1): 25-33, Jan. 1997.

(Continued)

*Primary Examiner* — Alton Pryor
(74) *Attorney, Agent, or Firm* — Fish & Richardson P.C.

(57) ABSTRACT

The invention describes an isolate of a fluorescent pseudomonad of the species *Pseudomonas azotoformans*, strain F30A, which has been deposited at Deutsche Sammlung von Mikroorganismen and Zellkulturen GmbH and has been assigned accession number DSM 22077, which is capable of enhancing seed germination, seedling establishment, plant emergence, plant growth and/or the yields of crops treated with the isolate. Accordingly the invention further comprises the use of this pseudomonad for enhancement of plant emergence and growth and agricultural compositions comprising the pseudomonad.

19 Claims, 21 Drawing Sheets

(56) References Cited

OTHER PUBLICATIONS

Howie and Echandi, "Rhizobacteria: Influence of cultivar and soil type on plant growth and yield of potato," *Soil Biology and Biochemistry*, 15(2):127-132, 1983.
Hsueh et al., "Outbreak of *Pseudomonas fluorescens* Bacteremia among Oncology Patients," *J Clin Microbiol.* 36(10): 2914-2917, Oct. 1998.
Kloepper and Schroth, "Plant growth promoting rhizobacteria on radishes," *Proc. 4th Int. Conference on Plant Pathogenic Bacteria*, pp. 879-882, Aug. 27-Sep. 2, 1978.
Kloepper et al., "Effects of rhizosphere colonization by plant growth-promoting rhizobacteria on potato plant development and yield," *Phytopathology*, 70(11): 1078-1082, 1980.
Kloepper et al., "Enhanced plant growth by siderophores produced by plant growth promoting rhizobacteria," *Nature*, 286:885-886, Aug. 1980.
Kropp et al., "Increased emergence of spring wheat after inoculation with *Pseudomonas chlororaphis* isolate 2E3 under field and laboratory conditions," *Biol Fertil Soils* 23: 200-206, 1996.
Levenfors et al., "Biological control of snow mould (Microdochium nivale) in winter cereals by *Pseudomonas brassicacearum*, MA250," *BioControl.*, 53(4): 651-665, 2008.
Loon, "Plant responses to plant growth-promotoing rhizobacteria," *Eur J Plant Pathol.*, 119:243-254, 2007.
Loper and Buyer, "Siderophores in microbial interactions on plant surfaces," *Molecular Plant-Microbe Interactions*, 4(1): 5-13, 1991.
Lucy et al., "Applications of free living plant growth-promoting rihizobateria," *Antonie van Leeuwenhoek* 86(1): 1-25, Jul. 2004.
Lugtenberg and Kamilova, "Plant-Growth-Promoting Rhizobacteria," *Annual Review of Microbiology* vol. 63: 541-556, Oct. 2009.
Maeng and Khudairi, "Studies on the flowering mechanism in Lemna. I. Amino acids changes during flower induction," *Physiol. Plant*, 28(2): 264-270, Apr. 1973.
Micsinai et al., "Rhizome-associated bacterial communities of healthy and declining reed stands in Lake Velencei, Hungary," *Hydrobiologia* 506: 707-713, 2003.
O'Sullivan and O'Gara, "Traits of fluorescent *Pseudomonas* spp. involved in suppression of plant root pathogens," *Microbiol Mol Biol Rev.* 56: 662-676, 1992.
Patten and Glick, "Bacterial biosynthesis of indole-3-acetic acid," *Can. J. Microbiol.*, 42(3):207-220, 1996.
Piao et al., "Changes in acetylene reduction activities and effects of inoculated rhizosphere nitrogen-fixing bacteria on rice," *Biology and Fertiliy of Soils*, 41(5):371-378, Jul. 2005.
Stanier et al., "The aerobic *pseudomonads*: a taxonomic study," *J Gen Microbiol.*, 43(2):159-271, May 1966.
Suslow and Schroth, "Rhizobacteria of sugar beets: Effects of seed application and root colonization on yield," *Phytopathology* 72:199-206, 1982.
Urashima et al., "Growth Promotion of Spinach by Fluorescent *Pseudomonas* Strains under Application of Organic Materials," *Soil Science & Plant Nutrition*, 51:841-847, 2005.
Vivekananthan et al., "Microbially induced defense related proteins against postharvest anthracnose infection in mango," *Crop Protection* 23:11, 1061-1067, 2004.
Wei et al., "*Pseudomonas fluorescens* Encodes the Crohn's Disease-Associated 12 Sequence and T-Cell Superantigen," *Infect Immun.*, 70(12): 6567-6575, Dec. 2002.
Weller, "Biological Control of Soilborne Plant Pathogens in the Rhizosphere with Bacteria," *Annual Review of Phytopathology*, 26:379-407, Sep. 1988.
International Search Report for PCT/SE2010/051468, mailed Mar. 4, 2011, 5 pages.
International Preliminary Report on Patentability and Written Opinion for PCT/SE2010/051468, issued Jun. 26, 2012, 5 pages.
Supplementary European Search Report for Application No. EP10839904 completed Apr. 11, 2013, 5 pages.

\* cited by examiner

FLUORESCENT PSEUDOMONAD OF THE SPECIES *PSEUDOMONAS AZOTOFORMANS* FOR ENHANCEMENT OF PLANT EMERGENCE AND GROWTH

This application is the U.S. national stage under 35 U.S.C. §371 of International Application Number PCT/SE2010/051468, filed on 22 Dec. 2010, which claims priority to U.S. Application Ser. No. 61/289,058, filed on 22 Dec. 2009, the entire contents of which are hereby incorporated by reference.

FIELD OF INVENTION

The present invention is directed to the field of promotion of plant emergence and plant growth. More specifically the invention is directed to a novel strain of *Pseudomonas azotoformans*, denoted F30A, which has been deposited at Deutsche Sammlung von Mikroorganismen and Zellkulturen GmbH and has been assigned accession number DSM 22077, its use as a plant emergence and plant growth promoting agent, and compositions and methods for such use.

BACKGROUND OF THE INVENTION

The rhizosphere bacteria (rhizobacteria) with beneficial effects on plant growth are often termed PGPR (Plant Growth-Promoting Rhizobacteria) and benefit the crop plant during various stages of its growth from sowing/planting until the harvest. Fluorescent pseudomonads in soil and rhizosphere have in numerous studies been demonstrated to exert plant growth promotion effects in several agricultural crops (Kloepper et al., 1980 a, b; Brisbane et al., 1989; DeFreitas and Germida 1991) and also to suppress plant diseases (Hemning, 1990, O'Sullivan and O'Gara, 1992, Weller, 1988, Hökeberg et al., 1997).

Under experimental conditions several fluorescent pseudomonads have been verified as potential agents to increase emergence and yield of agricultural crops, such as wheat (Kropp et al., 1996), mustard (Deshwal et al., 2006), sugar beet (Suslow and Schroth 1982), potato (Kloepper et al., 1980; Howie and Echandi, 1983), radish (Kloepper and Schroth 1978; Davies and Whitbread 1989) and spinach (Urashima et al., 2006). Several mechanisms connected to their plant growth promoting activity are well studied and described. These, among others, include root colonization ability (Benizri et al., 2001), capacity to produce a wide range of enzymes and hormones (Vivekananthan et al., 2004; Lucy et al., 2004, Patten and Glick 1996; García de Salamone et al., 2001) as well as other metabolites with often antimicrobial activity (Loper and Buyer 1991; Dowling and O'Gara 1994). Examples of patents/patent applications covering different areas of their activity are also available and involve mostly strains/isolates with biocontrol properties. Patent/patent applications on fluorescent pseudomonads with plant growth promoting properties cover most often an active component (bacterial strain) of the invention in combination with description of screening and test methods needed in order to select desired isolate(s). The following patent applications, which are hereby incorporated, provide some examples on the inventions covering fluorescent pseudomonads with plant growth promoting and/or biocontrol properties: WO/1987/000194, US1996/5503652, WO0051435, US1996/5503651, US2002/6447770, and US2002/6495362.

Despite the literature and patent/patent applications listed above, there is, so far no other isolate belonging to the species of *Pseudomonas azotoformans* that has been shown and proven to be able to consistently improve emergence, growth and yield of many important agricultural crops during several years of field experiments. In contrary, a previously studied soil-originating isolate of *Pseudomonas azotoformans* did not show any significant growth promoting effects in experiments with rice (Piao et al., 2005). The only brief information on plant growth promoting properties of isolates of *Pseudomonas azotoformans*, which concerns rhizome-associated bacterial communities of healthy reed stands in Lake Velencei, Hungary (Micsinai et al., 2003), is not based on any experimental data confirming its plant growth promoting properties.

SUMMARY OF THE INVENTION

The object of the present invention is to provide a novel strain of a fluorescent pseudomonad, which expresses plant emergence and/or plant growth promotion in several crops of agricultural importance. This object is obtained by the exceptional isolate of fluorescent pseudomonads from the species *Pseudomonas azotoformans*, denoted strain F30A. Strains of *Pseudomonas azotoformans* have previously never reported for plant growth promoting properties. This isolate provides significant plant emergence and growth promotion after it is applied to different crops, which are cultivated, both under greenhouse and field conditions. Moreover, based on the literature data available its effect is consistently more stable and repeatable than any other previously documented plant growth promoting microbial agent. A biologically pure strain of *Pseudomonas azotoformans*, strain F30A, has been deposited at Deutsche Sammlung von Mikroorganismen and Zellkulturen GmbH and has been assigned accession number DSM 22077.

The invention is therefore directed to a biologically pure strain of *Pseudomonas azotoformans*, strain F30A, which has been deposited at Deutsche Sammlung von Mikroorganismen und Zellkulturen GmbH and has been assigned accession number DSM 22077. The invention is also directed to a supernatant obtained from a culture of a biologically pure strain of *Pseudomonas azotoformans*, strain F30A, which has been deposited at Deutsche Sammlung von Mikroorganismen und Zellkulturen GmbH and has been assigned accession number DSM 22077.

The invention is also directed to the use of the biologically pure strain of *Pseudomonas azotoformans*, strain F30A, or a supernatant thereof, for enhancing seed germination, plant emergence and/or plant growth. Said seed and/or plant may e.g. be dicotyledonous or monocotyledonous.

The invention is also directed to a fermentation product of a biologically pure strain of *Pseudomonas azotoformans*, strain F30A.

The invention is also directed to an agricultural composition comprising a biologically pure strain of *Pseudomonas azotoformans*, strain F30A, or a supernatant thereof, optionally in combination with one or more liquid and/or solid carrier(s). The agricultural composition may further comprise one or more additional plant growth promoting microorganisms, bio-control microorganisms, organic fertilizers and/or agrochemicals.

The invention is further directed to a method for enhancing seed germination, plant emergence and/or plant growth comprising the step of applying a fermentation product or an agricultural composition as defined herein to a seed, a plant and/or the environment surrounding said seed or plant. The application may e.g. be made to the roots of a plant. The application may be made before and/or after the emergence of plant roots. The fermentation product or the agricultural composition may alternatively be applied to plant vegetative propagation units. The fermentation product or the agricultural composition may also be applied to plant vegetative propagation units or to plant growing media surrounding seeds and/or plants. The plant may be, or the seed may develop into, a monocotyledonous plant or a dicotyledonous plant.

The invention is also directed to a method for preparing an agricultural composition as defined herein, comprising the step of mixing said *Pseudomonas azotoformans*, strain F30A, or said supernatant with one or more liquid or solid carrier(s) and, optionally, one or more additional plant growth promoting microorganisms, bio-control microorganisms, organic fertilizers and/or agrochemicals.

DETAILED DESCRIPTION OF THE INVENTION

Plant Growth-Promoting Agent of the Invention

Figure 1:
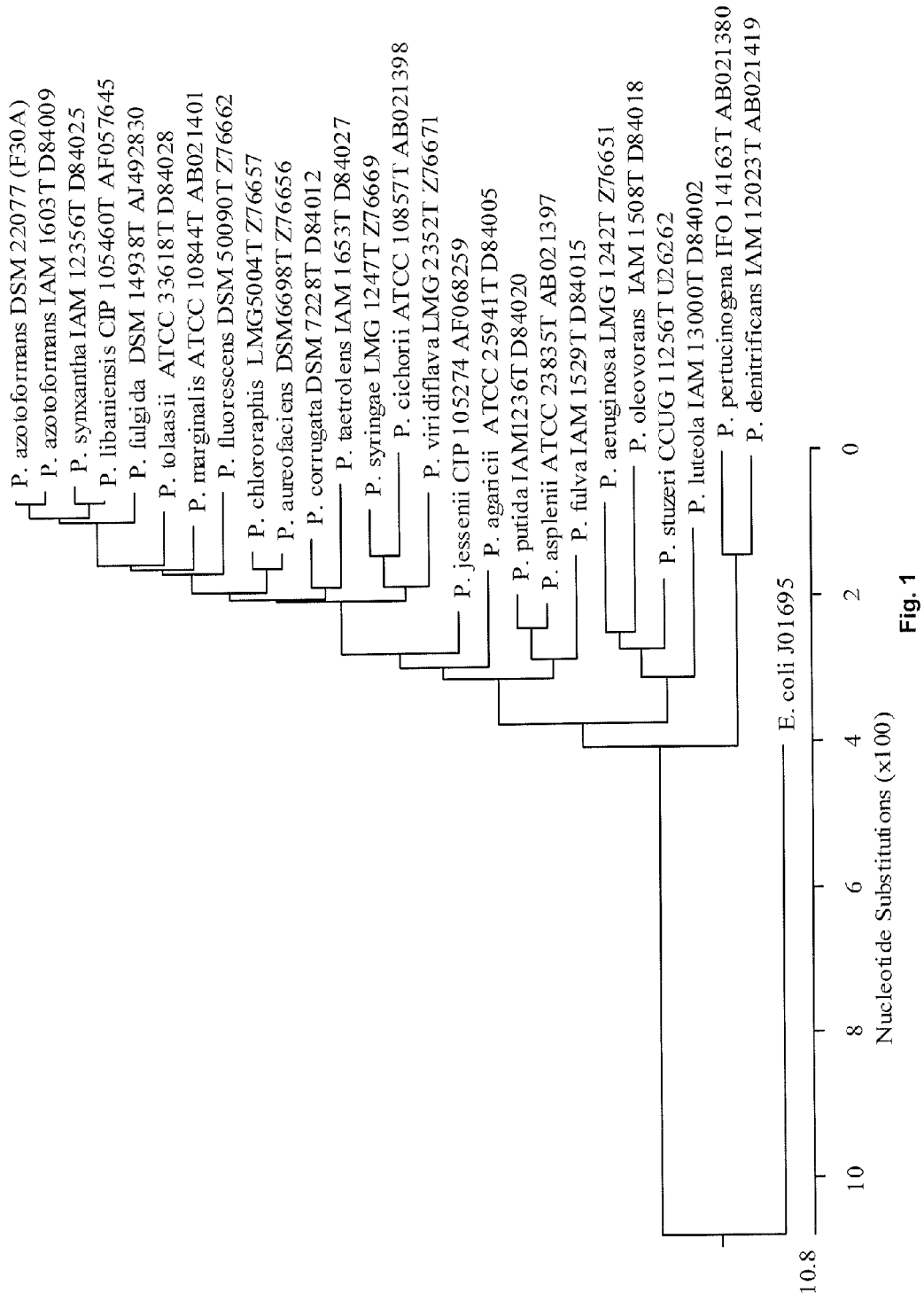
FIG. 1. Taxonomical position of the isolate F30A in comparison to the strains representing 25 various species of *Pseudomonas* and to one reference strain of *E. coli* (Gene Bank accession no. J01695) based on alignment of 1390 nucleotides of the 16S rDNA.

The present invention is directed to a novel strain of *Pseudomonas azotoformans*, strain F30A, which has been deposited Dec. 3, 2008, at Deutsche Sammlung von Mikroorganismen and Zellkulturen GmbH (Inhoffenstraße 7B; D-38124 Braunschweig; Germany) and has been assigned accession number DSM 22077. The depositor is Lantmännen BioAgri AB (P.O. Box 914; 751 09 Uppsala; Sweden). The F30A strain of the invention is a biologically pure strain.

The novel strain of *Pseudomonas azotoformans*, strain F30A, is in the below denoted also as the "isolate", the "agent" or *Pseudomonas azotoformans* F30A. *Pseudomonas azotoformans* may in the below be abbreviated as *P. azotoformans*. Also *Pseudomonas azotoformans*, strain F30A, may in the below simply be denoted as "F30A".

The plant growth promoting *Pseudomonas azotoformans* F30A of the invention comprises a biologically pure strain of a fluorescent Pseudomonad, which has the following specific identifying characteristics: (i) the isolate is a root-associated Gram-negative bacterium, a member of the *P. fluorescens* linage and it has a specific Biolog GM utilization profile distinct from the closest relatives; the selection and identification characters will be given below; (ii) the isolate has other unique morphological, biochemical and metabolic characters that are described below as well as an ability of nitrogen fixation, phosphorous solubilisation and sulphur solubilisation/oxidization (iii) the isolate enhances seed germination, plant growth and/or yield of at least the agricultural crops belonging to the following plant families: Amaranthaceae, Brassicaceae, Solanaceae, Astraceae, Apiaceae, Fabaceae, Rosacea, Cucurbitaceae, Lamiaceae, Aliaceae as well as enhances root formation and growth of tree plantlets in plant nurseries. Detailed examples of such effects will be given below.

The isolate of the invention has the following additional identifying characteristics: in the presence of the actively growing isolate intensive dark-green to nearly black pigment(s) are accumulated in organic culture media (PF agar, liquid media with soya peptone, wheat peptone and other plant peptones as a base substrates) and/or blue-green pigment(s) are accumulated in mineral culture media supplemented with glycerol (e.g. Lemna medium (Maeng and Khudairi, 1973). This pigment accumulation has not been reported in any other known pseudomonads. In addition, the isolate has a unique biochemical character with specific carbohydrate utilization profile tested by the Biolog GN system, which differed from those of the type strain of *Pseudomonas azotoformans* and from other closest related fluorescent pseudomonads.

The selection of the isolate of invention began by collecting whole plant samples including roots. Sample dilutions were derived from root pieces and plated on media suitable for isolation of bacteria. Bacterial colonies with different morphological characters were collected and maintained as −80° C. stocks. Liquid cultures on suitable microbiological substrates were derived from stocks and selection for plant growth promoting properties was performed by greenhouse bioassay(s) with wheat and sugar beet seeds inoculated with individual isolates. Isolates enhancing germination and plant growth were selected, identified and primary assessment of safety was performed in order to confirm their feasibility for larger scale greenhouse and field experiments.

Based on the set of morphological, biochemical and genetical characters, the selected isolate of invention is a Gram-negative flagellated bacterium and a member of the *P. fluorescens* linage, identified as a species of *Pseudomonas azotoformans* (FIG. 1). However, it has a unique utilization profile of the Biolog GN system in comparison with the type strain of *Pseudomonas azotoformans* IAM1603 and other closely related species of *Pseudomonas* (Table 1). In combination with traits listed in Table 1, the following features are very specific for the strain of invention: it utilizes sucrose and sebacic acid while members of the three closest related species do not, and it does not utilize xylitol and putrescine which are utilized by the members of the three closest related species.

TABLE 1

Crucial biochemical characters that differentiate between the isolate F30A and closely related type strains of *Pseudomonas azotoformans*, *P. libanensis* and *P. synxantha*.

| Character | F30A | *P. azotoformans* IAM1603 | *P. libanensis* CCM4841 | *P. synxantha* LMG2190 |
|---|---|---|---|---|
| Nitrate reduction | − | nt | $+^a$ | $+^a$ |
| Lecithinase | + | nt | $+^a$ | $d^a$ |
| Levan formation from sucrose | + | nt | $+^a$ | $-^a$ |
| Utilization of | + | + | + | − |
| i-Erythritol | + | − | − | − |
| Sucrose | − | + | + | + |
| Xylitol | + | + | + | − |
| Acetic acid | + | + | + | − |
| Cis-acetonic acid | + | − | + | + |
| Formic acid | + | + | + | − |
| D-galactonic acid lactone | − | + | + | + |
| α-hydroxybutyric acid | − | + | − | − |
| γ-hydroxybutyric acid | − | + | − | − |
| α-keto butyric acid | − | − | − | + |
| α-keto valeric acid | + | − | − | − |
| Sebacic acid | − | − | + | + |
| Succinamic acid | + | − | − | − |
| Glucuronamide | − | − | − | + |
| Glycyl-Laspartic acid | + | + | + | − |
| L-histidine | − | − | − | + |
| D-serine | + | + | − | + |
| L-threonine | + | + | + | − |
| Urocanic acid | − | + | + | + |
| Putrescine | | | | |

$^a$Data taken from Dabboussi et al., (1999) are based on characters of several strains and not only the strain LMG2190, which was used as a reference for Biolog test performed in MASE laboratories;
(−) negative,
(+) positive,
(d) divergent,
nt (not tested)

Other useful characters enabling identification of the isolate of invention are specific colony morphology on common bacteriological culture media such as: VPA—Vegetable Peptone Agar (10 g Vegetable Peptone Broth (Oxoid Ltd.), 15 g Agar Granulated (Difco Ltd) in 1000 ml distilled/deionised water); PF Agar (Difco Ltd, 38 g PF ready mix medium, 10 g glycerol in 1000 ml distilled/deionised water), accumulation of the previously described unique pigments.

Characteristic colony appearance of the isolate of invention is the best pronounced after 24 h of incubation at the temperature of 30° C. followed by additional 24-48 h incubation at room temperature (around 20-22° C.). When grown on VPA, colony edges are usually uneven and colony is slightly higher and denser in the middle. Colonies are compact, transparent, not slimy, denser and brownish in the middle with lighter bluish color at the edges and have typical shape resembling shell like structure.

Unique colony characters differentiating the isolate of invention from other isolates of fluorescent pseudomonads are also observed on PF agar after 5 to 8 days of incubation at room temperature. The colonies are white-greyish with a very clear yellow-brown small tip in the middle and rather regular edges.

During the culturing of the isolate of invention on PF agar the intensive green to nearly black pigment(s) accumulates in the agar.

In laboratory assays, the isolate of invention grows in a modified liquid mineral medium for *Pseudomonas* (Stanier et al. 1966) without any available nitrogen but supplemented with 2% of the suitable carbon source (e.g. glycerol), which indicates its ability of atmospheric nitrogen fixation. The liquid medium is inoculated with a loop of the overnight grown bacterial cells of the isolate of invention or the cells are suspended in 0.01 M magnesium sulphate and the cell suspension (0.1 ml per 5 ml liquid medium) is added to the mineral medium. Growth is monitored by optical density measurements (600 nm) for up to 5 days after inoculation. Optical density after 5 days is respectively 0.108 (loop inoculation) as compared to 0.069 at the start of the culture and 0.087 (cell suspension) as compared to 0.046 at the start of the culture. The measurements indicate the ability of the isolate of slow proliferation in the absence of nitrogen, which in turn indicates that the isolate of invention has the ability of nitrogen fixation.

Also, the isolate of invention solubilises phosphorus as well as oxidises thiosulphate and solubilises elemental sulphur. The assays are performed by inoculating the isolate of invention on agar plates supplemented with either insoluble phosphorous ($Ca_3(PO_4)_2$) or with thiosulphate/elemental sulphur. As the effect of solubilisation/oxidation of insoluble elements, clearing zone areas are formed around colonies of the isolate of invention.

An advantage of applying the PGPR isolate of the invention belonging to species of *Pseudomonas azotoformans*, instead of using isolates of the species *Pseudomonas fluorescens*, is that members of the *P. azotoformans* species have never been reported as possible human pathogens. In opposite to this, reports on pathogenicity of *P. fluorescens* towards human beings are available (see e.g. Franzetti et al., 1992, Hsueh et al., 1998; Wei et al., 2002).

Growth and Maintenance of the Isolate of Invention

The fluorescent pseudomonad isolate of invention (Pseudomonas azotoformans F30A) can be grown on any common suitable bacteriological medium (both solid and liquid). Some examples of suitable solidified media are Vegetable Peptone Agar (VPA) and *Pseudomonas* F Agar (PF Agar). Examples of liquid media are Vegetable Peptone Broth and all media with soy peptone as a major organic carbon source. At laboratory conditions, the isolate of invention grows well at any temperature suitable for typical environmental fluorescent pseudomonads i.e. from 15° C. to 30° C.; preferably in the temperature range from 23 to 27° C. Its growth is retarded by over 90% at the temperature of 37° C. The pH of the nutrient medium is preferably neutral ranging from pH 7.0 to 7.5.

Several organic substrates as e.g. Tryptic Soy Broth, Vegetable Peptone Broth as well as Plant Peptone, Wheat Peptone and Soy Peptone Broths support the excellent efficacy as well as production of the high biomass of the isolate of the invention. The greenhouse trials performed with two bioassay systems; root/soil application (iceberg lettuce) and seed application (spinach); allowed the selection of the MPS0 substrate (Levenfors et al., 2008), which was the most flexible for application in these various agricultural systems. However, for the isolate of invention the fermentation time should be 40 to 48 h and not shorter. In order to detect biological activity of the isolate of invention, other organic substrates are, though, also appropriate for its fermentation and the isolate of invention might, also, be cultured on the rotary shaker (120 rpm, 40-48 h, room temperature). In order to obtain satisfactory efficacy, fermentation of the biologically active product of the isolate of invention is, however, recommended to be performed at the pH ranges of 7.0 to 7.5 and temperature ranges of about 15-30° C., such as 20-28° C., most preferably about 23-27° C.

For efficacy trials, a fermentation product of the isolate of invention was usually fermented according to the standard fermentation protocol (pH 7.0; 20° C.) or according to the optimised fermentation protocol (pH 7.25 and 25° C.) during the entire process of fermentation (see experimental section for the respective protocols). Additionally, bacterial cells obtained by means of centrifugation of the standard or the optimised fermentation product of the isolate of invention (8000 rpm, 15 min) and afterwards formulated in appropriate inorganic or organic agriculturally compatible carriers were, also, tested in selected trials. All these types of preparations of a fermentation product are suitable for use for seed germination or plant growth enhancement and in the methods of the invention.

To ensure it remains stable, the isolate of invention may be maintained either as freeze-dried stock culture or as deep-freeze at −80° C. stock culture in a mixture of 20% VPB and 30% glycerol. For fermentation, and in order to start liquid cultures, generally about 100 µl of the deep-freeze stock culture is transferred into 100 ml of any 50% strength organic liquid media suitable for bacterial growth, i.e. 50% strength TSB, and grown on a rotary shaker (120 rpm; 22-25° C.; at most 24 h). For other experimental purposes small amount of the deep-freeze stock culture of the isolate F30A might also be plated on any solid organic substrate medium suitable for bacterial growth and stored for a period not longer than two weeks at +4° C.

Plant Growth Promoting Activity

The biologically pure *Pseudomonas azotoformans* F30A isolate of the invention has the ability to enhance the seed germination, plant emergence and establishment, promote establishment and formation of flowers and/or enhance plant growth, thereby increasing the yields of plant crops. One aspect of the invention therefore relates to the use of the isolate of the invention for enhancing seed germination, plant emergence and/or plant growth. The plants may be monocotyledonous or dicotyledonous plants or the seed may be able to develop into either of these two types of plants.

The isolate of the invention enhances germination, emergence, flowering and/or improves growth and yield in the above mentioned agricultural crops in a range from about 4 to over 50%.

The examples presented below demonstrate the plant growth promoting activity of the *Pseudomonas azotoformans* F30A of the invention. Table 2 shows field trials data on summarized average yield increase after application of the isolate of invention as either seed, root/soil (transplant) or tuber treatment in crops of interest in a range of field or commercial greenhouse trials, performed in Sweden, during four consecutive growing seasons. Examples 1 to 18 clearly show an exceptional plant growth promoting potential of the isolate of invention in commercial field/greenhouse trials or in growth chamber experiments (wheat, Poaceae) when applied as a seed-, tuber-root- and soil-drench treatment into non-infected plant systems. Moreover, the plant growth promoting effect of the isolate of invention is observed after application to seed infested with seed-borne pathogens e.g *Fusarium* spp. in wheat (example 1). Such an effect may be a result of escape from the infection by stimulating seed germination and the growth of the newly emerged seedling. Thereby, the susceptible phase for the plant is overcome more rapidly and infection could be avoided. Moreover, the wide range of the plant growth promoting activity of the isolate of the invention is not affected by the soil type (field and greenhouse trials were all performed in various type of soils and greenhouse substrates) and also not by the environmental conditions such as climate (the isolate of invention was confirmed to be effective in promoting plant growth in a wide range of crops during several growing seasons with different temperature and precipitation patterns).

TABLE 2

Yield increase after application of the *Pseudomonas azotoformans* F30A in a number of vegetable crops as compared to the yield obtained from untreated control plots. Different treatment methods adjusted to the commercial requirements were used to apply isolate F30A. Experiments were performed as field- or commercial greenhouse trials during four consecutive growing seasons. The mean yield increase data are average from number of field trials performed.

| Crop | Application | Mean yield increase | No. of field trials | Remark |
|---|---|---|---|---|
| Spinach | Seed | 19% | 17 | |
| Peas | Seed | 6% | 9 | |
| Rucola/Rocket | Seed | 13% | 3 | |
| Broccoli | Transplant | 52% | 6 | |
| Iceberg lettuce | Transplant | 23% | 6 | |
| Lettuce | Transplant | 16% | 1 | |
| Potted lettuce | Transplant | 15% | 5 | Commercial greenhouse trial |
| Swedish turnip | Transplant | 14% | 3 | |
| Cabbage | Transplant | 17% | 4 | *Brassica oleracea* var. *capitata* |
| Strawberry | Transplant | 46% | 1 | |
| Pepper | Transplant | 16% | 1 | Greenhouse trial |
| New potato | Tuber | 9% | 5 | |
| Late potato | Tuber | 4% | 8 | |

Also, the supernatant of the isolate of invention (the cell-free fermentation product of the *P. azotoformans* F30A obtained after centrifugation (8000 rpm or higher, 20 min or longer) and additional filter-sterilization (0.2 µm)) enhances germination, emergence plant growth and/or yield.

Examples 1, 2 and 4 show the potential of the supernatant of the isolate of invention to significantly enhance emergence of spring wheat and spinach as well as yield of spring wheat and iceberg lettuce.

Application and Application Specifications of the Isolate of the Invention

Furthermore, it is an object of this invention to make available effective preparations/formulations comprising the *Pseudomonas azotoformans* F30A of the invention and/or its supernatant that are effective in enhancing seed germination and/or in improving plant growth and/or yield of crops of agricultural importance when applied as treatment of seeds, vegetative propagation units, roots, soil and/or other plant growing media and/or as drench. Thus, the present invention provides also agricultural compositions, which comprise the plant growth-promoting *Pseudomonas azotoformans* F30A of the invention and/or its supernatant optionally in combination with one or more agriculturally compatible carrier(s) allowing liquid formulation of the isolate of the invention, or agriculturally compatible carrier(s) allowing dry or solid preparations/formulations of the isolate of this invention.

The isolate of invention is useful in enhancing seed germination and plant emergence, improving density of crop stands, promoting plant flowering and plant growth and improving the yields of greenhouse and field dicotyledonous and monocotyledonous agricultural crops from e.g. the following plant families: Amaranthaceae (i.e. sugar beet, spinach, mangold wurzel), Solanaceae (i.e. potato, pepper), Fabaceae (i.e. pea), Brassicaceae (i.e. ruccola, broccoli, various cabbage varieties, Swedish turnip, oilseed rape), Astraceae (i.e. various lettuce varieties), Apiaceae (i.e. carrot), Rosacea (i.e. strawberries) and Poaceae (i.e. wheat), Cucurbitaceae (i.e. cucumber) Lamiaceae (i.e. oregano), Aliaceae (i.e. chives). The isolate of invention is also useful in improving root formation and/or plant growth of tree plantlets in various plant nurseries (i.e. Scots pines of the family Pinaceae).

In order to enhance seed germination and/or plant emergence, improve density of crop stands, promote plant flowering and/or growth and/or finally improve the yields, crops are grown in the presence of a define amount of the of the plant growth promoting isolate of the invention i.e. *Pseudomonas azotoformans* F30A, where the define amount of the plant growth promoting isolate is described as a quantity of the isolate which significantly enhances seed germination, improves density of crop stands, promotes plant flowering and growth and finally improves the yield when compared to the a none-treated control. The amount of the isolate of invention needed to obtain desired effects differs between crops and depends on the application method of the isolate of invention (seed treatment of seed-sown dicotyledonous and monocotyledonous crops, vegetative propagation unit (tuber, bulb, rhizome etc.) treatment in potato and other vegetative propagated crops as well as soil/root/drench-treatments of vegetable transplants and other crops plantlets). Ten to 100 ml of the product of the *Pseudomonas azotoformans* F30A (between $7.5 \times 10^8$ to $7.5 \times 10^9$-colony forming units per ml) per one kilogram seed, 10 to 20 ml per each transplanted plantlet (root/soil/drench) and 100 µl to 1 ml per each vegetative propagation unit, e.g. potato tuber, is usually recommended to obtain the desired effect of plant growth promotion. However, the amount of the isolate of invention should preferably be determined on a case by case basis for different crop/application method combinations.

Optionally, 10 to 100 ml of the cell-free supernatant of the *Pseudomonas azotoformans* F30A per one kilogram seed, 10 to 20 ml per each transplanted plantlet (root/soil/drench) and 100 µl to 1 ml per each vegetative propagation unit, e.g. potato tuber, is usually recommended to obtain the desired effect of plant growth promotion. However, the amount of the isolate of invention should preferably be determined on a case-by-case basis for different crop/application method combinations.

The *Pseudomonas azotoformans* F30A cells of the invention may be applied to seeds, plants and/or the environment surrounding the seed or plant (e.g. to the soil) in the form of a fermentation product or in the form of an agricultural composition in order to enhance seed germination and/or plant growth.

One aspect of the invention is therefore directed to a fermentation product (i.e. bacterial cells together with their used growth medium) of the biologically pure strain of *Pseudomonas azotoformans* F30A.

Another aspect of the invention is directed to a supernatant obtained from a culture of a biologically pure strain of *Pseudomonas azotoformans*, strain F30A, which has been deposited at Deutsche Sammlung von Mikroorganismen and Zellkulturen GmbH and has been assigned accession number DSM 22077. Such a supernatant may be used in all aspects of the invention instead of the bacterial cells or the fermentation product of the cells.

Yet another aspect of the invention is therefore directed to an agricultural composition comprising of the biologically pure strain of *Pseudomonas azotoformans* F30A, or a supernatant of a culture thereof optionally in combination with one or more liquid and/or solid carrier(s). An agricultural composition is a composition that, without jeopardizing the biological effect of the active ingredient, makes practical application and use in agricultural systems possible. An agricultural composition of the invention comprises the pure culture/fermentation product of *Pseudomonas azotoformans* F30A, its cells (e.g. prepared by removing the culture medium by centrifugation and optionally washing the cells with e.g. a suitable buffer) and/or its cell free supernatant optionally formulated with any suitable agriculturally acceptable liquid and/or solid carrier, which does not negatively influence the isolate activity and the growth of the crop to be applied to. Further optional constituents of such an agricultural composition are exemplified elsewhere herein.

Also, the growth medium may also be removed from a bacterial culture of *Pseudomonas azotoformans* F30A, e.g. by centrifugation, and the bacterial cells resuspended in water of other liquid media or buffers known in the art before application to plants, seeds or soil. As the supernatant itself comprises active substances produced by the *Pseudomonas azotoformans* F30A, also the supernatant may be used instead of the bacterial cells in all aspects of the invention.

Yet another aspect of the invention is directed to a method for preparing an agricultural composition comprising *Pseudomonas azotoformans* F30A comprising the step of mixing said *Pseudomonas azotoformans* F30A, or a supernatant obtained from a culture thereof with one or more liquid and/or solid carrier(s) and, optionally, one or more additional plant growth promoting microorganisms, bio-control microorganisms, organic fertilizers and/or agrochemicals. The skilled person is well aware of suitable such agents.

The *Pseudomonas azotoformans* F30A cells may also be provided to seeds, plants and/or the environment surrounding the seed or plant (e.g. to the soil) in the form of dried cells, such freeze-dried, spray dried, vacuum dried or fluidized bed dried cells. Such a composition may further comprise one or more suitable carrier(s).

An agricultural composition, comprising *Pseudomonas azotoformans* F30A or a culture supernatant thereof, may also comprise further microorganisms, such as biocontrol microorganisms, additives and/or adjuvants having e.g. plant growth promoting, plant protective (i.e. bio-control) or technically beneficial effects, in order to further enhance the performance of the agricultural composition.

The pure culture/fermentation product/supernatant of the *Pseudomonas azotoformans* F30A of the invention may directly be applied to seeds, tubers or plantlets of crops and/or the environment surrounding the seed or plant (e.g. to the soil) to be treated as well it may constitute a part of an agricultural composition suitable for above specified applications.

The pure culture/fermentation product of *Pseudomonas azotoformans* F30A, its cells (e.g. prepared by removing the culture medium by centrifugation and optionally washing the cells with e.g. a suitable buffer) or its cell free supernatant may optionally be mixed and formulated with any suitable agriculturally acceptable carrier, which does not negatively influence the isolate activity and the growth of the crop to be applied to. Examples of the suitable carriers are organics based on soy peptone or other appropriate compounds mixed with physiological salts, methylcellulose, dextrin as well as minerals. Suitable carriers for agricultural use for the application of bacteria to plants are known to the skilled person. When the *Pseudomonas azotoformans* F30A is applied in the form of a suspension or an emulsion, this suspension or emulsion may also comprise one or more commercially available additives, such as surfactants, wetting agents etc. Also, the *Pseudomonas azotoformans* F30A may preferably be used together with other plant growth-promoting agents (see e.g. Lugtenberg and Kamilova, 2009 for suitable plant growth-promoting agents), biological control agents (see e.g. Compant et al., 2005 for suitable biological control agents), organic fertilizers and/or agrochemicals. Therefore, a further aspect of the invention is directed to an agricultural composition comprising *Pseudomonas azotoformans* F30A further comprising one or more additional plant growth promoting microorganisms, bio-control microorganisms and/or agrochemicals.

The biological control agents and agrochemicals could have e.g. fungicidal, bactericidal, nematicidal, insecticidal, herbicidal or bird repellent effects. The agrochemicals could also be plant fertilizers or plant regulators. Examples of full compatibility between the isolate of invention and some selected agrochemicals, organic fertilizers and biological control agents are given in Example 18 below.

Examples of application areas for the isolate of the invention, application specifications and defined effective amounts are given below. The amount of the isolate of invention that is effective for a specific application and a specific agricultural crop is preferably determined on a case by case basis.

For seed application, preferably, the bacterial cells, the fermentation product (i.e. bacterial cells together with their used growth medium) or agricultural composition comprising *Pseudomonas azotoformans* F30A (comprising e.g. about $10^7$-$10^{11}$ colony forming units $ml^{-1}$) is applied by commercially available seed treatment equipment in suitable doses depending on the crop. Suitable carriers, additives and/or adjuvants (which are well-known to the skilled person) may be added at appropriate concentrations in order to improve the effect, adherence, storage stability and technical performance of the formulation during and after seed coating. Moreover, the *Pseudomonas azotoformans* F30A cells may be formulated with the carriers or carrier combinations by conventionally available methods in order to obtain solid preparations. Such preparations are then suspended in liquid carriers, resulting in a cell concentration of about $10^7$-$10^{10}$ colony forming units per ml.

For application to soil, turf or other plant growth media or for root/soil treatment of transplants/plantlets, watering, spraying or drenching of transplant racks may be used for distribution of the *Pseudomonas azotoformans* F30A to the desired site. The bacteria might also be distributed through watering, spraying or nutrient supply systems when used for treatment of commercial greenhouse crops. The pure culture or fermentation product, or dilutions of any of these, or agricultural composition comprising *Pseudomonas azotoformans* F30A (preferably about $10^6$-$10^{10}$ colony forming units $ml^{-1}$) is applied in dosages suitable for each crop and application technique. Suitable carriers might be added at appropriate concentrations in order to e.g. improve adherence of the bacteria to the plant roots.

For application to various tubers, bulbs etc., spray coating with conventional machinery (centralised coating at time of sorting) or tuber/bulb etc. drenching prior to planting or at planting site are applicable. The pure culture or the fermentation product of *Pseudomonas azotoformans* F30A (preferably about $10^9$-$10^{10}$ colony forming units $ml^{-1}$) is applied in dosages of approximately about 0.1-10 ml per one tuber. Suitable carriers may be added at appropriate concentrations in order to e.g. improve adherence of the bacteria to the tubers.

The *Pseudomonas azotoformans* F30A of the invention enhances seed and/or tuber/plant vegetative propagation unit germination, improves density of crop stands, promotes plant growth and/or significantly improves the yields of greenhouse and field dicotyledonous and/or monocotyledonous agricultural crops. The ability to promote growth and improve yield is, in addition, not influenced by soil type and climatic conditions and the type of substrate used for plant cultivation. Over 60 field trials have been performed on different soils (from sand to clay) during four years, representing different climatic conditions. In addition, 10 commercial greenhouse tests have been performed, plus numerous other greenhouse experiments, using peat based planting soil.

The invention further comprises a description of specific identification characters. Results of the identification and characterization of the isolate of the invention are described herein.

A further aspect of the invention comprises specific fermentation parameters, applicable for a range of laboratory and industrial substrates that could be used for the cultivation of the plant growth-promoting agent of the invention.

The present invention also relates to a method for enhancing seed germination, plant emergence and/or plant growth comprising the step of applying the *Pseudomonas azotoformans* F30A bacterial cells, or a fermentation product or an agricultural composition comprising *Pseudomonas azotoformans* F30A to a seed, a plant and/or the environment surrounding a seed, or a plant. The *Pseudomonas azotoformans* F30A may in such a method e.g. be applied to the roots of a plant. Alternatively, the *Pseudomonas azotoformans* F30A in such a method may be applied to soil before and/or after the emergence of plant roots or to plant growing media surrounding seeds and/or plants. The *Pseudomonas azotoformans* F30A bacterial cells, or a fermentation product or an agricultural composition comprising *Pseudomonas azotoformans* F30A may alternatively be applied to plant vegetative propagation units or applied to plant growing media surrounding seeds and/or plants. Of course a combination of any of the above methods for application may be used. The seed or the plant treated with the *Pseudomonas azotoformans* F30A bacterial cells, or a fermentation product or an agricultural composition comprising *Pseudomonas azotoformans* F30A may be a monocotyledonous plant or a dicotyledonous plant or a seed that will develop into such a plant.

Additional objects and advantages of the invention will become undoubtedly apparent from the following detailed description of this invention. However, the detailed description and specific examples are only given to illustrate the preferred embodiments of this invention and various changes and modifications within the scope of this invention will be apparent to those skilled on the issues concerning subject of the invention.

EXPERIMENTAL SECTION

The following examples additionally illustrate the advantages of this invention and should not limit the scope of the invention as it is defined by the claims.

For the application in all described examples, if not specified otherwise, the isolate of invention was fermented according to either standard (pH 7.0, 20° C.) or optimized (pH 7.25, 25° C.) fermentation protocol with the MPS0 culture medium (Levenfors et al., 2008) as the growing substrate. Prior to the fermentation, the culture medium is sterilized. An appropriate amount of carbon source (e.g. glycerol, fructose, sucrose, glucose) is added and oxygen and pH electrodes are calibrated. The fermentor is thereafter inoculated with an appropriate amount of start culture of the isolate of invention grown in any appropriate bacterial liquid substrate. The fermentation parameters (oxygen supply and pH) are controlled throughout the fermentation procedure. A suitable antifoam substrate is added when required. The fermentation product is harvested 2 to 3 h after the measured oxygen consumption indicates the shift in secondary metabolism (generally after 40 to 48 h). Non-diluted or diluted with tap water, fermentation product comprising cells of the isolate in the MPS0 culture medium or its cell-free supernatant, and preferably not more than 3 months old were applied to seeds, potato tubers or to roots/soil of tested agri- and horticultural crops. Certain trials were, also, performed with non-diluted or diluted bacterial cells of the isolate of invention obtained by means of centrifugation of its standard or optimized fermentation product (8000 rpm, 15 min) and afterwards formulated in appropriate inorganic or organic agriculturally compatible carriers.

The first seven examples describe greenhouse/growth chamber trials, including commercial trials, demonstrating enhancement of seed germination and plant emergence of wheat, spinach and oilseed rape as well as the yield increase of iceberg lettuce green mass, increase of the fruit weight of pepper, yield increase of selected potted herbs and yield increase of cucumber after application of the isolate of the invention.

Example 1

Enhancement of Plant Emergence and Plant Growth—Spring Wheat Greenhouse Trials

Prior to sowing, spring wheat seeds (30 g) were treated with the fermentation product of the isolate of invention fermented according to the standard fermentation protocol, with its bacterial cells diluted with tap water or with cell-free supernatant diluted with tap water (300 ml/kg seeds), followed by mixing the seeds with fermentation product/bacterial cells/supernatant for a period of around 2 min and overnight drying. If needed, seeds were afterwards stored for a period for up to 2 weeks before setting up the trials.

Four pots with 50 seeds each were afterwards sown for each treatment, respectively and placed in a growth chamber with the temperature of 18-20° C. (none infected seed lot) or 10-12° C. (seed lot infected with *Fusarium* and with *Microdochium* fungi) and a light period of 14 hours. Non-sterile commercial peat mixture "Enhetsjord" (Gerhardson et al., 1985) was used in all trials. Emerged plants were counted 5-6 days after placing pots at the temperature of 18-20° C. and 12-14 days at 10-12° C. After additional 12 to 18 days plants were cut at a distance of around 0.5 cm from the soil surface and the dry weight of shoots was measured after overnight drying at 105° C. in order to estimate the increase of the plant mass after treatment with isolate of invention.

Figure 2:
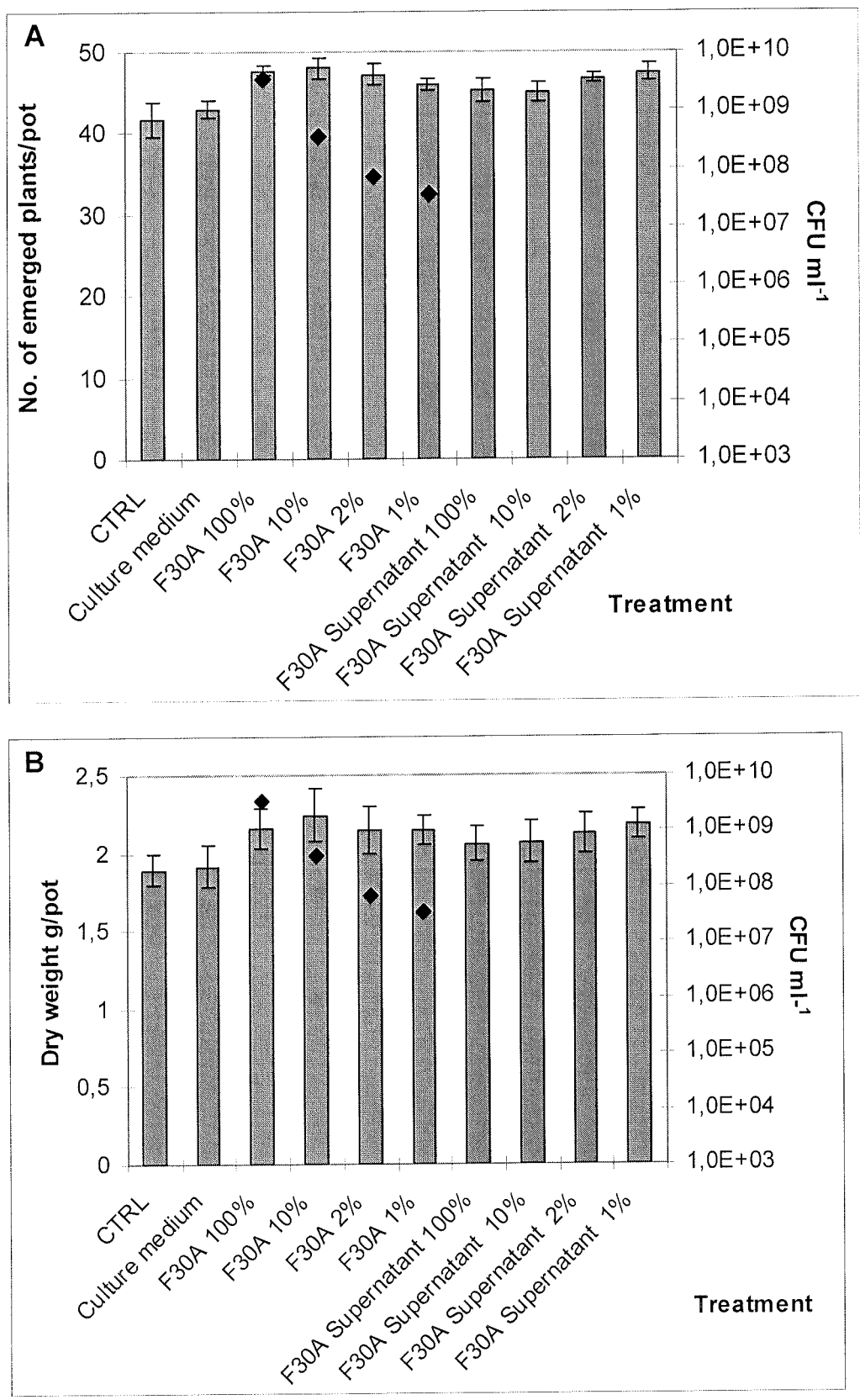
FIG. 2. Emergence (A) and dry weight (B) of spring wheat (non-infected seed lot) after seed application with the F30A fermentation product and its supernatant at different concentrations. Greenhouse experiment. Squares indicate CFU per ml. Error bars represent standard error of the mean (n=4).
Figure 3:
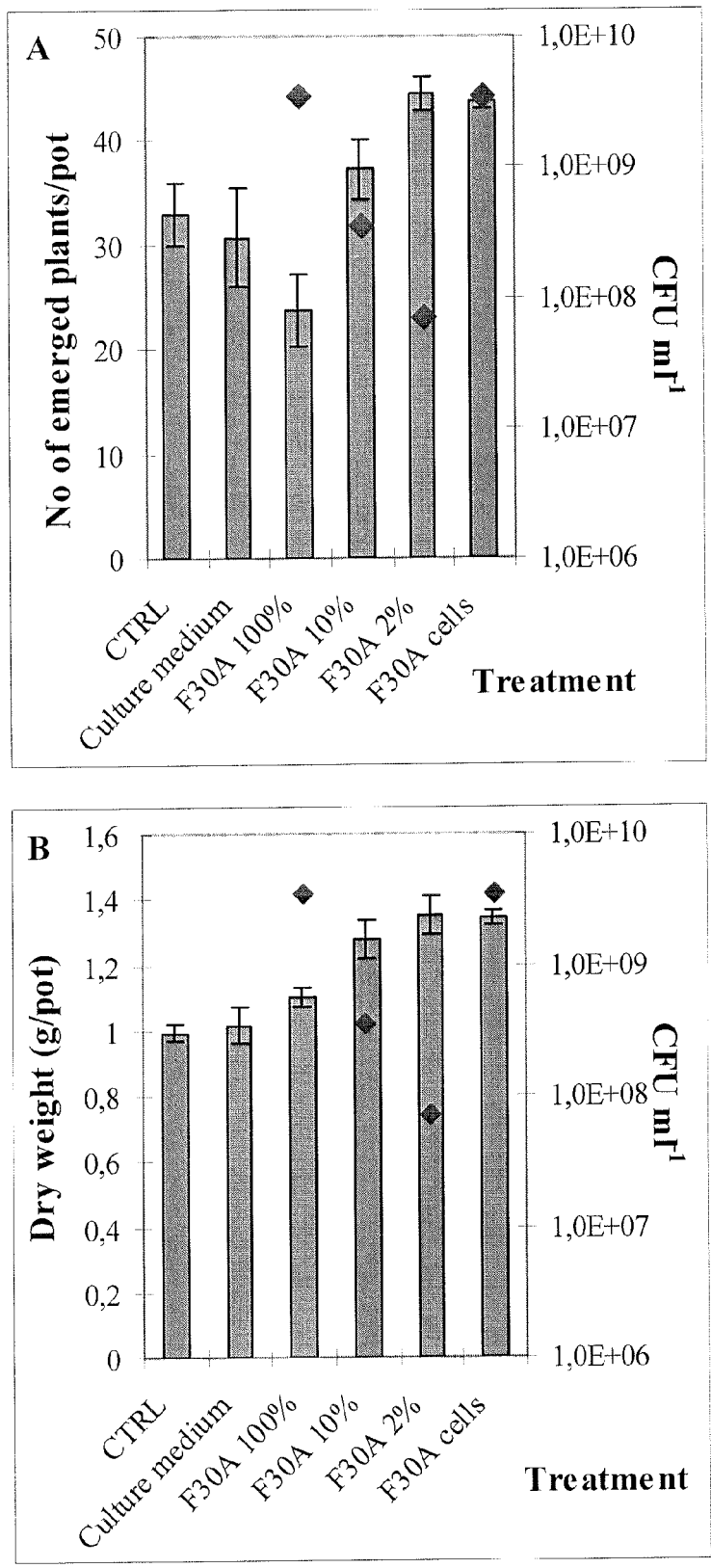
FIG. 3. Emergence (A) and dry weight (B) of spring wheat (non-infected seed lot) after seed application with the F30A fermentation product in different concentrations and of the F30A cells suspended in physiological salt solution. Greenhouse experiment. Squares indicate CFU per ml. Error bars represent standard error of the mean (n=4).

FIGS. 2 and 3 show the enhancement of plant emergence of spring wheat after treatment with the isolate of invention at different concentrations and the effect of its application on the dry weight of wheat tested in growth chambers experiments with respectively none-infected (FIG. 2) and infected seed lots (FIG. 3) of spring wheat. At appropriate concentrations, emergence was enhanced by 10 to 15% (none infected seed lot) and by 12 to 35% (infected seed lot). Dry weight estimated around 20 days after sowing was also significantly increased; 13-18% (none infected seed lot) and 10-36% (infected seed lot). In addition, FIG. 2 shows the enhancement of spring wheat emergence and dry weight after application of the supernatant of the isolate of invention at different concentrations. At appropriate concentrations, emergence was enhanced by 5 to 10% and dry weight by 8 to 15%

The results presented confirm the isolate usefulness in application to both non-infected and infected seed lots as a solely plant growth promotion agent. The unique property of the isolate F30A to strongly enhance seed germination and emergence results in the process of escape from the disease, improves the kernel growth and overall plant condition expressed as an amount of the dry plant matter produced over period of the experiment (around 20 days)

Example 2

Enhancement of Plant Emergence—Spinach Greenhouse Trials

Prior to the sowing spinach seeds (3 to 5 g) were treated with the fermentation products of the isolate of invention, or with its cell-free supernatant, fermented according to the standard protocol (batch no. FOM115) or the optimized protocol (batch no. FOM139) or with bacterial cells, which were obtained from the respective fermentation products and afterwards rehydrated in tap water (300 ml/kg seeds). Seeds were then mixed with respective bacterial treatments for a period of around 2 min and overnight drying. If needed seeds were afterwards stored for a period for up to 2 weeks before setting up the trials.

Four pots with 25 seeds each were afterwards sown for each treatment, respectively and placed in growth chambers with the temperature of 12-14° C. a light period of 14 hours. Non-sterile commercial peat mixture "Enhetsjord" (Gerhardson et al., 1985) was used in all trials. Emerged spinach plants were continuously counted over a period of around 8-10 days, starting from the day 7 after sowing. The plant counts obtained day 9 are used in all below presented results.

Figure 4:
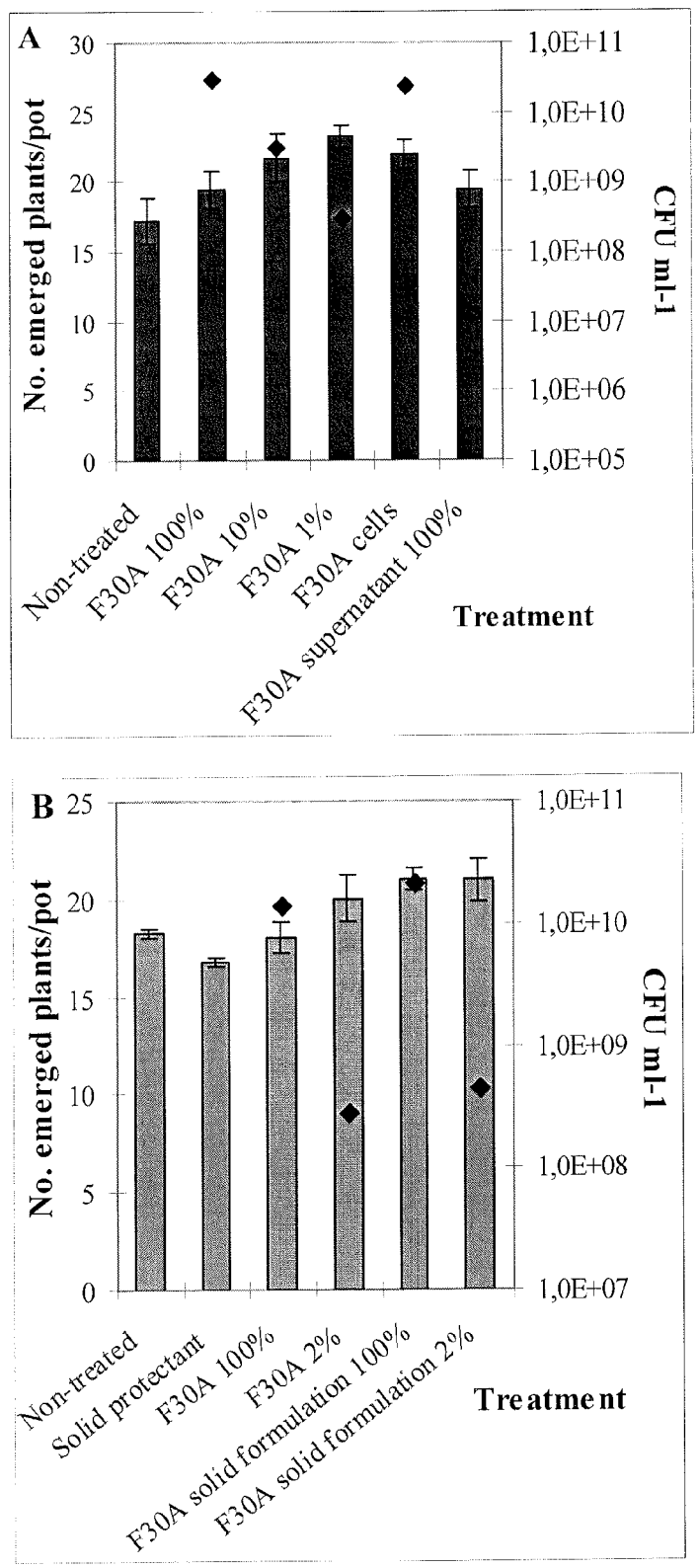
FIG. 4. Emergence of spinach after seed application with the F30A fermentation product at different concentrations, the F30A cells suspended in tap water and the isolate supernatant. Results from two different fermentation product batches: batch FOM115 (A), and batch FOM139 (B). Greenhouse experiment. Squares indicate CFU per ml. Error bars represent standard error of the mean (n=4).

FIG. 4 shows the enhancement of emergence of spinach after treatment with the isolate of invention at different concentrations and with its supernatant (FIG. 4A) and after the treatment with the selected solid preparation of the isolate (FIG. 4B). At appropriate concentrations, seed treatment with fermentation product resulted in enhancement of emergence of up to 35%. The application of non-diluted supernatant resulted in 13% better emergence when compared to non-treated control. An application of solid cell preparation was also effective in enhancement of emergence; at tested concentrations up to 15% more plants emerged after treating seeds with this preparation, re-hydrated in physiological salt solution.

Examples from greenhouse trials clearly show a significant ability of the strain of invention to enhance germination and emergence of spinach. The enhancement is expressed in the presence of the fermentation product of the isolate as well as in the presence of cells suspended in the physiological salt solution or water or dry cell preparations, re-hydrated in physiological salt solutions. The detectable emergence enhancement, as shown by given examples, is usually in a range of 10 to 40% and depends on the concentration of the products applied to spinach seeds.

Example 3

Enhancement of Plant Emergence—Oilseed Rape Greenhouse Trials

Prior to sowing the seeds of oilseed rape cv. Joplin (10-20 g) were treated with the fermentation product of the isolate of invention fermented according to the modified protocol and dried overnight. Seeds were treated with four doses (10, 20, 40 and 60 ml per kg seeds) of the fermentation product containing respectively $5.0 \times 10^7$, $5.0 \times 10^8$ and $5.0 \times 10^9$ cfu of the isolate of invention per ml.

Six pots with 25 seeds each were afterwards sown for each treatment, respectively and placed in growth chambers with the temperature of 12-14° C. a light period of 14 hours. Nonsterile commercial peat mixture was used in all trials.

Emerged oilseed rape plants were continuously counted over a period of around 4-5 days, starting from the day 5 after sowing. The plant counts obtained day 6 were used for estimation of emergence enhancement. Application of the fermentation product with $5.0 \times 10^7$ per ml (0.5%) gave the most uniform enhancement of the oilseed rape emergence independently of the dose, with on average 31% emergence enhancement. A larger variation was detected when the doses 20, 40 and 60 ml per kg of the fermentation product $5.0 \times 10^8$ per ml (5%) and $5.0 \times 10^9$ per ml (50%) were applied to seeds (Table 3).

TABLE 3

Enhancement of oilseed rape emergence after application of the isolate of invention at three concentrations and four doses (n = 6).

| Dose | Treatment/Emerged plants, day 6 | | |
|---|---|---|---|
| | $5.0 \times 10^7$ per ml (0.5%) | $5.0 \times 10^8$ per ml (5%) | $5.0 \times 10^9$ per ml (50%) |
| 0 ml (non-treated) | 16.0 +/− 2.3 | 16.0 +/− 2.3 | 16.0 +/− 2.3 |
| 10 ml | 22.0 +/− 1.1 | 18.3 +/− 2.5 | 23.8 +/− 0.4 |
| 20 ml | 20.3 +/− 1.0 | 20.7 +/− 1.0 | 18.8 +/− 3.2 |
| 40 ml | 20.3 +/− 1.1 | 22.3 +/− 0.7 | 20.7 +/− 1.5 |
| 60 ml | 21.5 +/− 0.8 | 17.3 +/− 3.7 | 23.6 +/− 1.2 |

Example 4

The Enhancement of Iceberg Lettuce Yield—Root Application, Greenhouse Trials Trays were placed in the greenhouse/growth chambers (18° C. and a light period of 14 h) and after a period of around 2 weeks plantlets were transplanted to pots (1 plantlet/pot) with the same peat-based substrate. Pots were placed at the greenhouse/growth chamber for additional 4 to 6 days and then 10 to 20 ml of the fermentation product of the isolate of invention fermented according to the standard or to the optimized fermentation protocol as well as other bacterial solutions comprising *Pseudomonas azotoformans* F30A (e.g. bacterial cells rehydrated in appropriate inorganic and organic solvents) and its supernatant was applied nearby roots. Pots were kept for a subsequent period of around 2-3 weeks in the greenhouse/growth chamber. Lettuce plants were then cut at the distance of around 0.5 cm from the soil surface and weighed in order to measure the green mass produced during the period of the trial.

Application of 10 ml of fermentation products or other preparations of the isolate of invention ($5 \times 10^9$-$4 \times 10^{10}$ colony forming units (cfu) per ml) as root/soil treatments into iceberg lettuce plantlets at transplantation resulted in exceptional enhancement of the lettuce growth and finally in higher green mass of the treated plants when compared to non-treated control plantlets.

Figure 5:
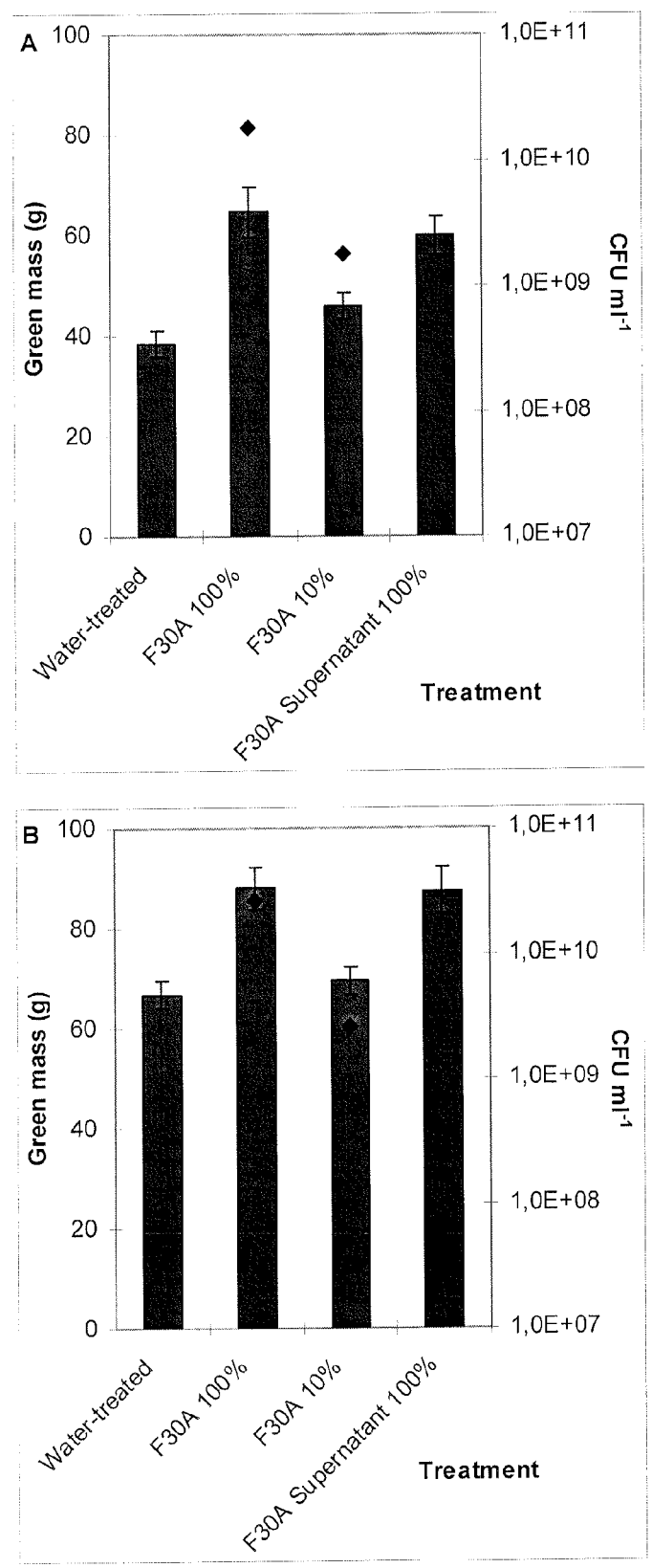
FIG. 5. Green mass yield of iceberg lettuce after root/soil application with the F30A fermentation product at different concentrations and after application of its supernatant. Two different fermentation product batches were used: batch FOM173 (A), and batch FOM176 (B). (A) and (B) represent two independent greenhouse experiments. Squares indicate CFU per ml. Error bars represent standard error of the mean (n=12).

FIG. 5 shows examples from two separate greenhouse experiments with two fermentation products of the isolate of invention and its supernatant (batch FOM173 and batch FOM176), both fermented according to the optimized protocol. The detected increase of the iceberg lettuce green mass was in a range 19 to 68% (greenhouse trial with fermentation batch 173) and 3 to 32% (greenhouse trial with fermentation batch 176). The application of the supernatant resulted in green mass increase by respectively 56% (batch 173) and 36% (batch 176).

Figure 6:
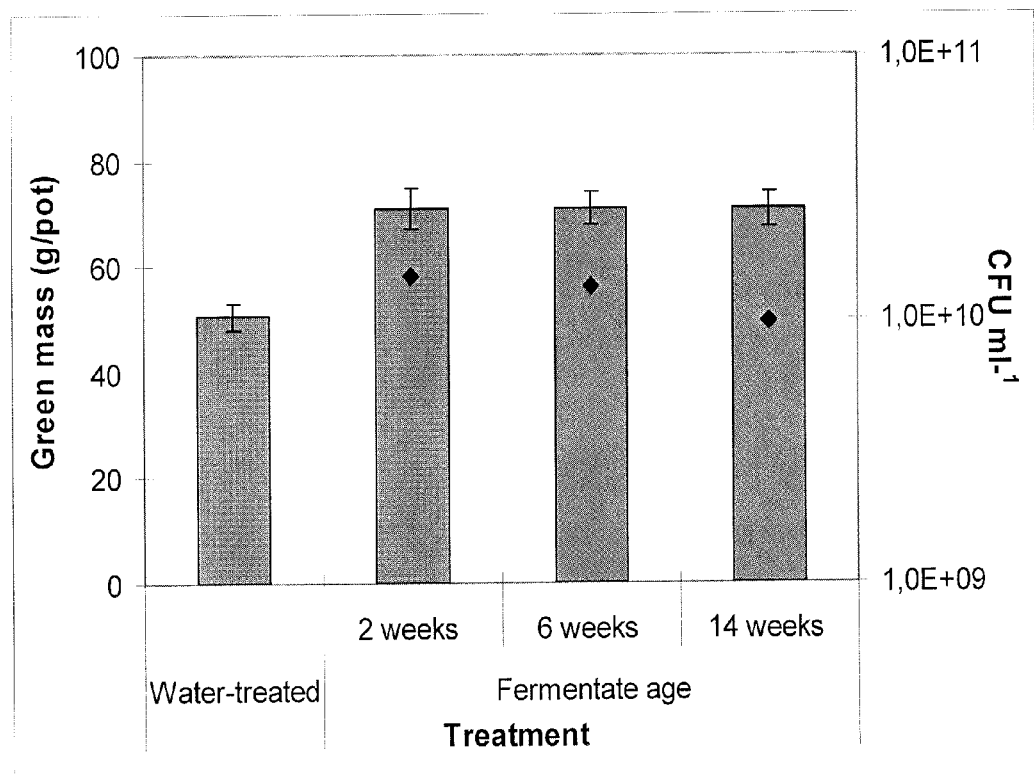
FIG. 6. Green mass yield of iceberg lettuce after root/soil application with stored fermentation product batches of F30A. Batch FOM203 had been stored in 4° C. for 2 weeks, batch FOM196 for 6 weeks and batch FOM192 for 14 weeks. Greenhouse experiment. Squares indicate CFU per ml. Error bars represent standard error of the mean (n=12).

Moreover, fermentation products of the isolate of invention have good storage stability; the efficacy of fermentation products stored for a period of up to 14 weeks at 4° C. were not affected by product storage. An exemplary greenhouse trial demonstrating the growth promotion of iceberg lettuce treated with 2, 6 and 14 weeks old fermentation products of the isolate of invention, which all were fermented according to the optimized protocol, is shown in FIG. 6. In this greenhouse trial, independently of the age of the fermentation product, the green mass of plants treated with the isolate of invention was increased by around 40%. Furthermore, the viable cell counts in the 14 weeks old fermentation product was around $1 \times 10^{10}$ cfu per ml when compared to 1.3 and $1.5 \times 10^{10}$ cfu per ml in respectively 6 and 2 weeks old fermentation products.

Example 5

The Enhancement of Pepper Yield—Root Application, Greenhouse Trial

In order to detect the growth promotion effect after root/soil application to transplants/plantlets pepper was used as the additional test crop. Pepper seeds were sown into pot trays with the commercial peat-based substrate. Trays were placed in the greenhouse/growth chambers (25° C. day; 20° C. night and a light period of 14 h) and after a period of around 3 weeks plantlets were transplanted to pots (1 plantlet/pot) with the same peat-based substrate. Pots were placed in the greenhouse/growth chamber for additional 4 to 6 days and then 10 ml of the fermentation product of the isolate of invention fermented according to the standard or to the optimized fermentation protocol as well as other bacterial solutions comprising *Pseudomonas azotoformans* F30A (e.g. bacterial cells rehydrated in appropriate inorganic and organic solvents) was applied nearby roots. Pots were kept for a subsequent period of up to 4 months in the greenhouse/growth chamber. Pepper fruits were harvested at two occasions and weighed in order to estimate the total fruit weight per each plant.

Figure 7:
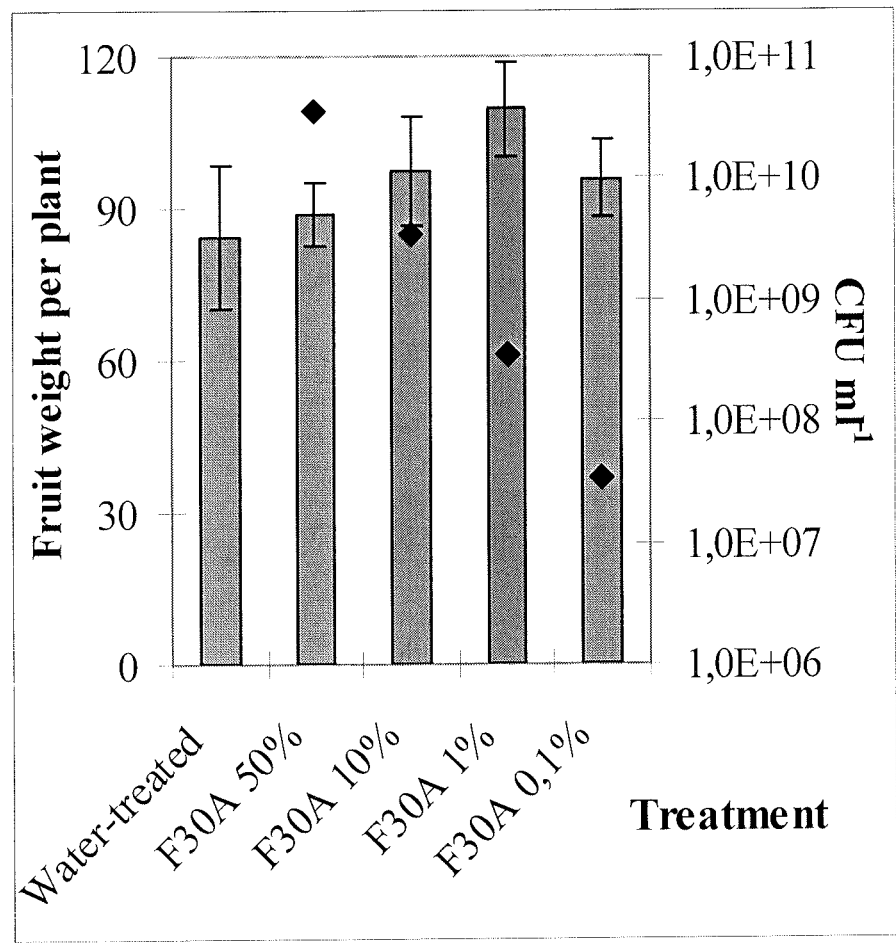
FIG. 7. Fruit yield of pepper after root/soil application with the F30A fermentation product (batch FOM076) in different concentrations. Greenhouse experiment. Squares indicate CFU per ml. Error bars represent standard error of the mean (n=8).

Application of 10 ml of fermentation products of the isolate of invention at varying concentrations from $3.5 \times 10^7$ to $3.5 \times 10^{10}$ cfu per ml as root/soil treatment into plugs of pepper plantlets at their transplantation resulted in higher average yield of the pepper fruits when compared to non-treated control plants. FIG. 7 shows yield increase of pepper fruits after pepper plantlets were treated with the fermentation product of the isolate of invention batch FOM076. The yield increases of 6 to 30% when compared to non-treated control was detected depending on the concentration of the isolate of invention during the treatment of pepper plantlets.

Example 6

The Enhancement of Mangold Wurzel, Coriander, Oregano and Chives Yield—Soil Application, Greenhouse Trial The following potted herbs: mangold wurzel, coriander, oregano and chives were sown in pots with a commercial soil substrate and using a commercially available sowing system. The soil surface in the pots (25 per each potted herb) was then sprayed with 10 ml of the fermentation product of the isolate of invention (approx. 1 to $3 \times 10^9$ cfu per ml) per one liter of soil substrate. Pots were placed in a commercial greenhouse used for cultivation of potted herbs and growing conditions were as normal for cultivation of potted herbs. Green mass of plants was measured after approximately one to two months depending on the potted herb.

The green mass of potted herbs treated with the isolate of invention was on average around 7% higher than the green mass of herbs harvested from untreated pots (Table 4). Additionally, plants looked greener and stronger.

TABLE 4

Green mass of potted herbs treated with the isolate of invention in comparison to the green mass of respective non-treated controls and the percent of mean yield increase (n = 25).

| Potted herb | Average green mass (g) | | Mean yield increase (%) |
| --- | --- | --- | --- |
| | Non-treated | F30A | |
| Coriander | 22.33 | 23.82 | 6.7 |
| Mangold (red) | 25.06 | 26.86 | 7.2 |
| Oregano | 19.17 | 20.64 | 7.7 |
| Chives | 22.09 | 23.56 | 6.7 |

Example 7

The Enhancement of Cucumber Yield—Root/Soil Application, Commercial Greenhouse Trial Prior to the treatment with the isolate of invention the cucumber transplants were planted in a commercial greenhouse with an area of 4600 m², according to the requirements for cucumber cultivation. The fermentation culture of the isolate of invention (20 liters; approximately $2\text{-}3 \times 10^9$ cfu per ml) was then mixed with 80 liters of water in the watering container and plants were treated with the mixture using a commercial watering system. The control were cucumbers cultivated in the same type of greenhouse; cultivation area of 5400 m²; treated with water. Both treatments were started and finished the same day, all growing parameters and other necessary practical measures such as fertilization were kept the same for both greenhouses. The cucumber yield was measured in kg per square meter of the greenhouse and additionally the number of harvested cucumbers per square meter was counted. During the harvest period 13.75 kg/m² and 344 cucumbers/m² were harvested from the greenhouse treated with the isolate of invention, as compared to 13.03 kg/m² and 326 cucumbers/m² from the greenhouse treated with water. The numbers correspond to the yield increase of 5.5% per m² in the greenhouse with the application of the isolate of invention.

Field Trials

The commercial field and greenhouse trials with the isolate of invention aimed to evaluate its potential to enhance seed germination and plant emergence as well as to improve plant coverage, plant growth, flowering and/or yield under natural conditions. Field experiments (altogether 82 field trials/commercial greenhouse trials) including some larger scale experiments (up to 1 ha) were performed during four growing seasons in a broad range of dicotyledonous crops of agricultural importance (see Table 2) and focused on evaluation of the plant growth promotion properties by using different measure parameters. The average mean yield increase data for crops, in which treatments with the isolate of invention resulted in significant yield improvement, are presented in Table 2.

The standard and optimized fermentation products of the isolate of invention were used in a vast number of field trials.

Three different application methods were used to treat a target crop with the isolate F30A. These were seed treatment, seed tuber treatment (potato) and root/soil treatment of transplants. The application method depended on and was adjusted to common practices used for each crop and most of the field trials have been situated in southern Sweden, the main area for vegetable and potato production in Sweden. Moreover, in all field experiments, common agricultural practices have been used in order to test the usefulness of the application of the isolate of invention in combination with other necessary measures, which must be undertaken to ensure a profitable harvest. Most trials were carried out following a fully randomized block design with four, or in some experiments five replicates. Data were analyzed by analysis of variance (ANOVA) and general linier model (GLM) in SAS/Stat (Statistical Analyses System). Emergence/plant establishment, number of flowers (strawberry) and yield/marketable yield has been scored in the trials.

Figure 8:
FIG. 8. Soil/root treatment of iceberg lettuce. Left pot: water control; right pot: F30A fermentation product.

Seed treatment of various crops with the isolate F30A resulted in yield increases of between 6 and 19% (Table 2). Furthermore, yields were often significantly higher or higher than these obtained after treatment with standard chemicals (see example 8 spinach and example 10 pea). The plant emergence was visibly enhanced when compared with plant emergence on plots with non-treated control and the effect was maintained throughout the growing season until harvest. Yield enhancement up to 40% was measured in some individual field trials. Also the root/soil treatment of transplants with the isolate F30A with the drench method resulted in a rapid and visible enhancement of the growth of treated plantlets, apparent already after a few days (example of the effect on the growth of lettuce from the greenhouse trials is shown in FIG. 8).

These effects were maintained throughout the growing season, resulted in earlier harvest and much higher yields than in control treatments. The yield increases after root/soil treatments with the isolate of invention depended on the crop and were on average between 17 and 52% (Table 2). The treatment of potato tubers resulted in yield enhancement of 4 to 9% (Table 2) with the highest relative yield increase of up to 25% recorded in some individual field trials with new potato.

Separate examples (examples 8-18) presented below will further demonstrate the usefulness of application of the isolate of invention in order to improve the yield in a range of crops of agricultural importance. Effects of the application of the isolate of invention to other crops are currently tested or will be subsequently evaluated. Therefore, the presented examples are not meant to limit the scope of this invention as it is defined by the claims.

Example 8

Figure 9:
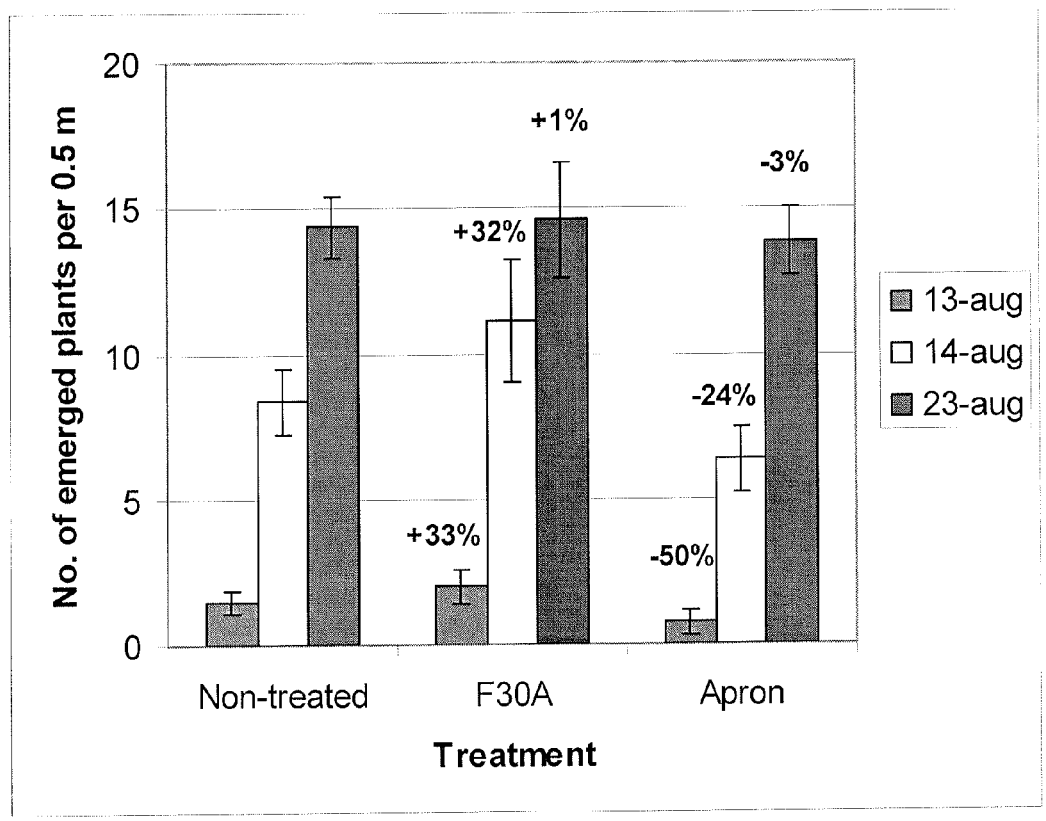
FIG. 9. Emergence of spinach in field experiment after seed application with the F30A fermentation product (batch FOM233). The emergence was recorded on three separate occasions. Percent increase/decrease of emergence, compared to non-treated control is indicated in the figure. Error bars represent standard error of the mean (n=4).

Enhancement of Plant Emergence and Yield—an Example from the Spinach Field Trials In spinach field trials with exception of large-scale trials, randomised block design with 4 to 5 repetitions was used to set up experiments. Seeds were sown in rows and every plot was usually 15 $m^2$. Yield was estimated at two occasions after harvesting representative plots of 0.25 $m^2$. Prior to beginning field trials seed lots of commercially used spinach varieties were treated with the fermentation product of the isolate of invention fermented according to the standard or to the optimized fermentation protocol and other appropriate treatments such as e.g. commercial fungicides were also applied to seeds. The two dosages of the isolate of invention were usually used in field trials; 300 ml/kg seed or 10 ml/kg seed. The dosage adjustment was done after dose-response greenhouse experiments and is suitable for industrial applications. Before sowing, seeds could be eventually stored according to standards used in common practices. The exemplary field trial presented here, which demonstrates enhancement of plant emergence as well as improvement of yield was performed in Southern Sweden. Spinach seeds were treated with a dosage of 10 ml/kg of the fermentation product of the isolate of invention (batch FOM233); controls were non-treated seeds and seeds treated with the standard dose of the chemical fungicide Apron. FIG. 9 shows the data on enhancement of plant emergence. Enhancement of emergence was especially significant at two first reading occasions when enhancement of emergence by 33 and 32% respectively was detected (FIG. 9).

Figure 10:
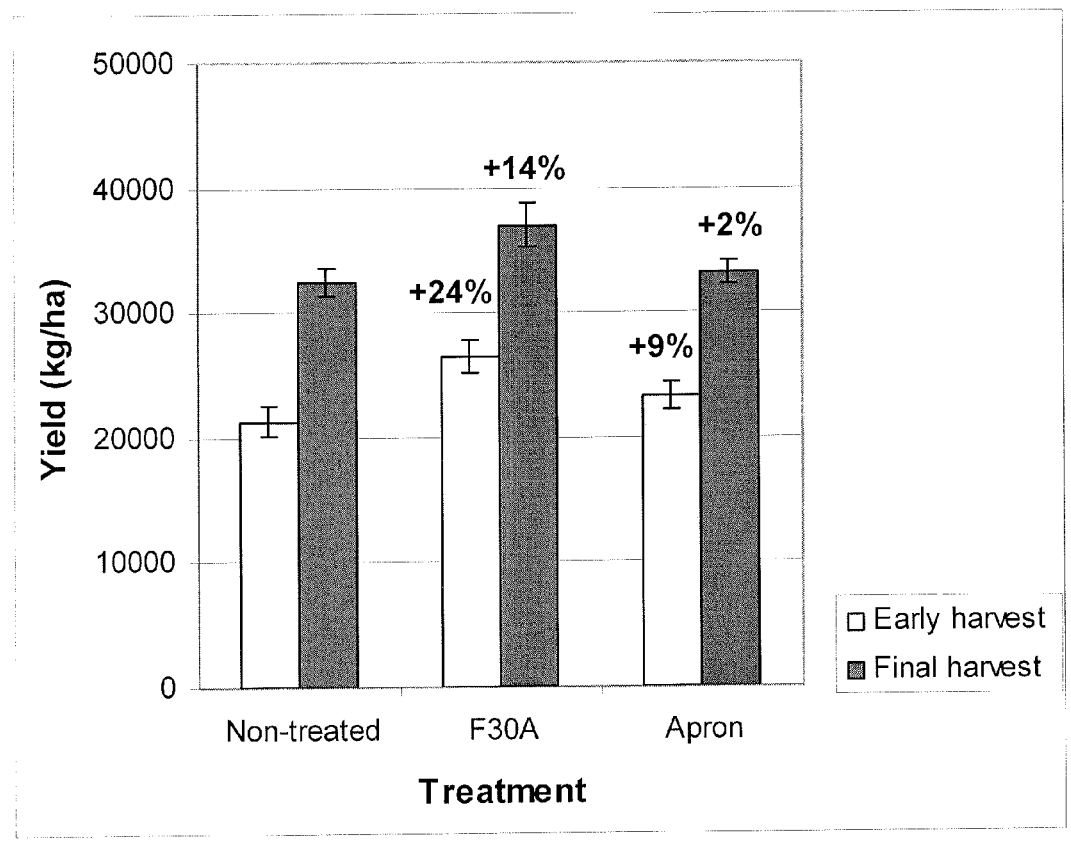
FIG. 10. Spinach yield in field experiment after seed application with the F30A fermentation product (batch FOM233). The yield was measured at two different time-points. Error bars represent standard error of the mean (n=4).

The enhancement of plant emergence visibly improved early plant coverage, which was clearly better than coverage obtained from non-treated seeds and seeds treated with the standard fungicide Apron. Additionally, plants after the treatment with the isolate of invention were stronger and bigger than these emerging from non-treated seeds or seeds treated with Apron. This resulted in significantly higher yields. FIG. 10 shows the yield increase in the presented example, in which yield was increased by 24% (early harvest) and 14% (final harvest), respectively.

Example 9

Enhancement of Plant Emergence and Yield—an Example of the Rocket Field Trials

Figure 11:
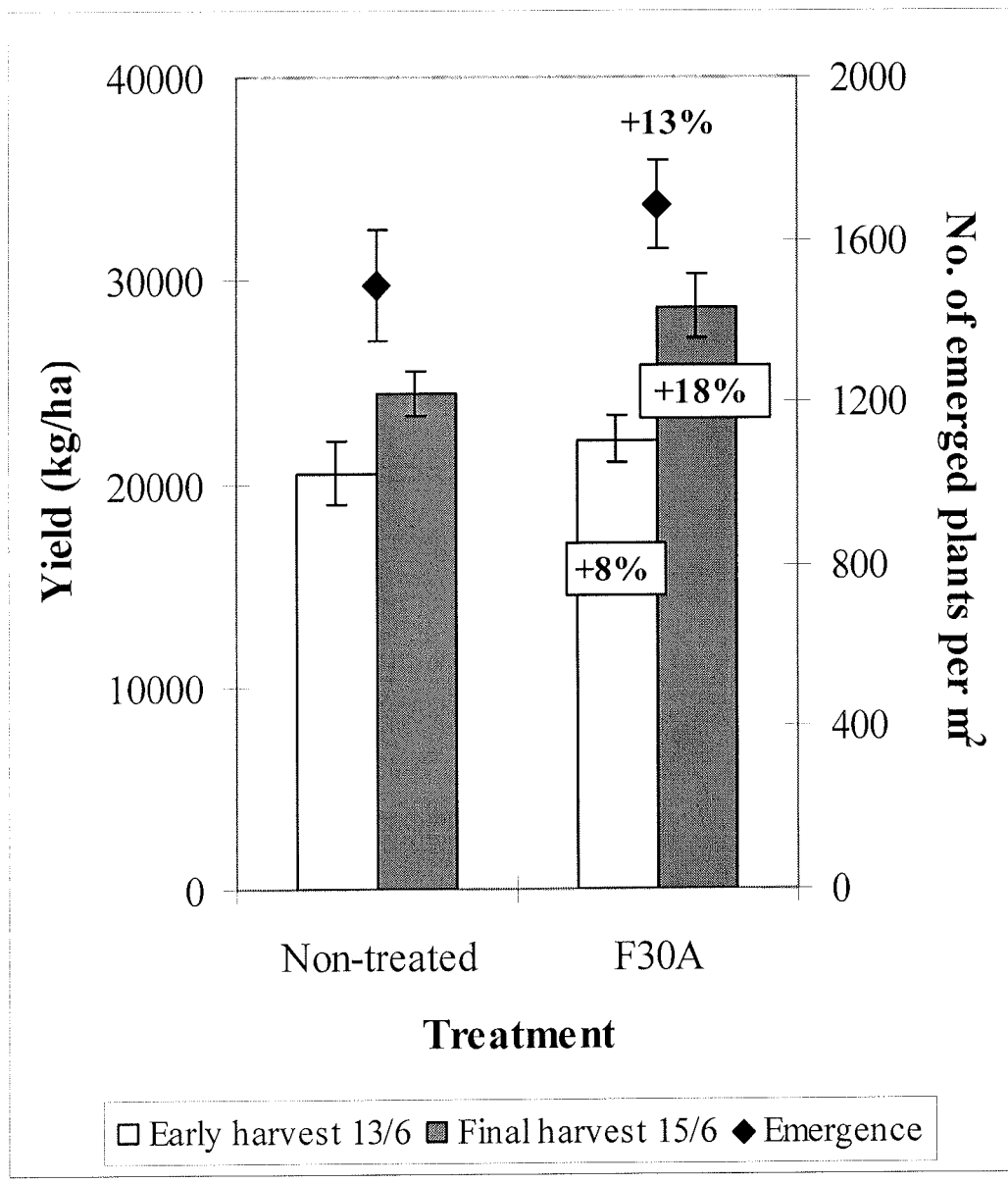
FIG. 11. Rocket yield (bars) at two occasions and emergence (squares) after seed application with the F30A fermentation product (batch FOM154) in field experiment. Error bars represent standard error of the mean (n=12).

Rocket field trials were performed in a similar way as the spinach trials. The experimental set up was adjusted according to agronomic practices at the trial site. Seeds were sown in rows with 6 cm space between and plots of around 4 $m^2$ were chosen as a standard. Yield was estimated at two occasions after randomly harvesting rocket in rows corresponding to each treatment; plants from 2 meter (n=2 or n=4) of the total row length of up to 55 meters were collected and weighed. Seed treatment was performed in a similar manner as for spinach; two dosages of the isolate of invention were usually used in field trials; 300 ml/kg seed or 100 ml/kg seed. An exemplary field trial demonstrating enhancement of plant emergence as well as improvement of rocket yield was performed in Southern Sweden. In this field trial rocket seeds were treated with a dosage of 300 ml/kg of the fermentation product of the isolate of invention (batch FOM154) fermented according to the optimized protocol; controls were non-treated seeds. FIG. 11 shows the data on enhancement of plant emergence of rocket and the yield increase after application of the isolate of invention. Emergence was enhanced by around 13% what resulted in yield increase of 8 to 18% depending on the harvest occasion (FIG. 11).

Example 10

Enhancement of Plant Emergence and Yield—an Example of the Pea Field Trials

Figure 12:
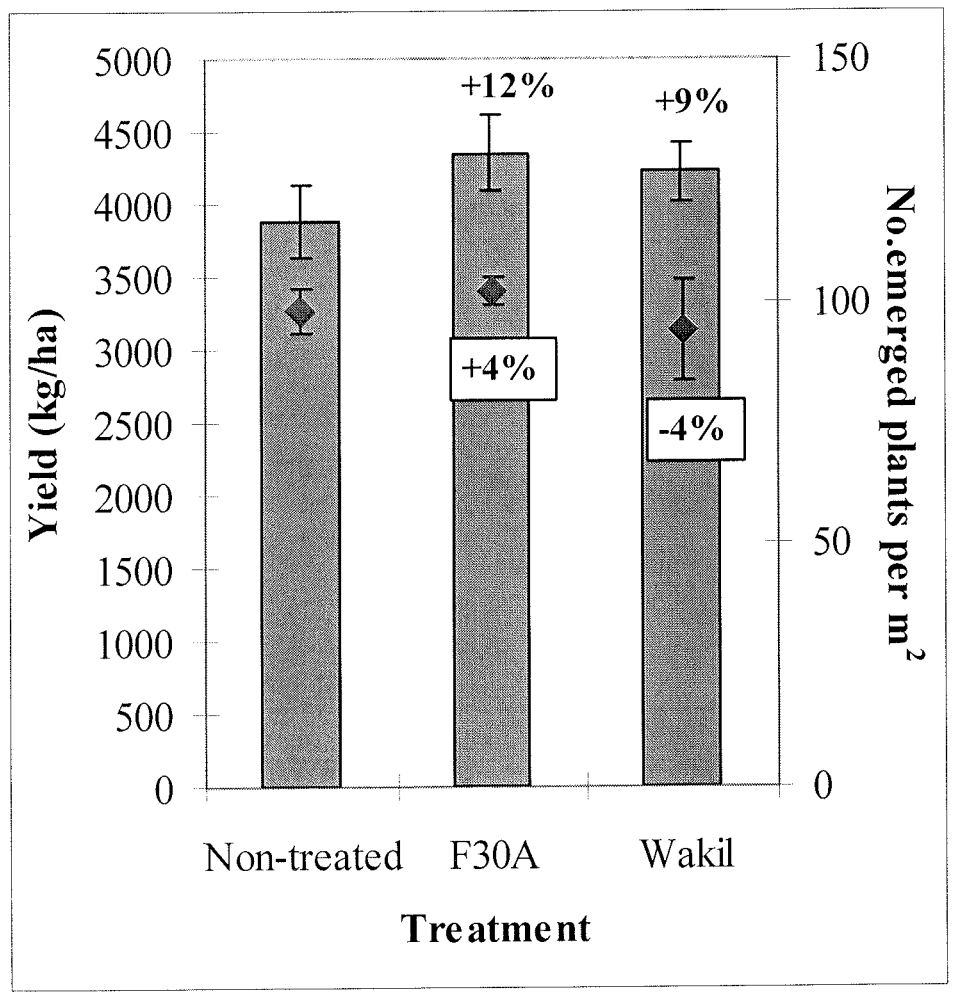
FIG. 12. Yield of vining peas after seed application with the F30A fermentation product (batch FOM150) in field experiment. Error bars represent standard error of the mean (n=4).

The same principles as for field trials with seed treatment of other crops were used in experiments with pea. Field trials were placed in Southern Sweden at commercial farms growing vining pea. 50 ml of the fermentation products were usually applied per kilogram seeds and a plot area of 15 $m^2$ was used most often. Yield was estimated after harvesting pea from the plot area of 10 $m^2$. The yield was recalculated to a tenderometer value of 100 (T 100) representing the same maturity stage for all harvested vining peas. An exemplary field trial demonstrating enhancement of plant emergence and improvement of pea yield was performed in Southern Sweden. Pea seeds were treated with a dosage of 50 ml/kg of the fermentation product of the isolate of invention fermented according to the optimized protocol (batch FOM150; around $9.25 \times 10^9$ cfu per ml); controls were non-treated seeds and seeds treated with the chemical fungicide Wakil. FIG. 12 shows the data on the yield increase, which was slightly better (3%) than after application of Wakil and 12% better when compared to non-treated control. Also plant emergence was enhanced by 4% when compared to non-treated control.

Example 11

Enhancement of Yield—an Example from the Carrot Field Trials

Figure 13:
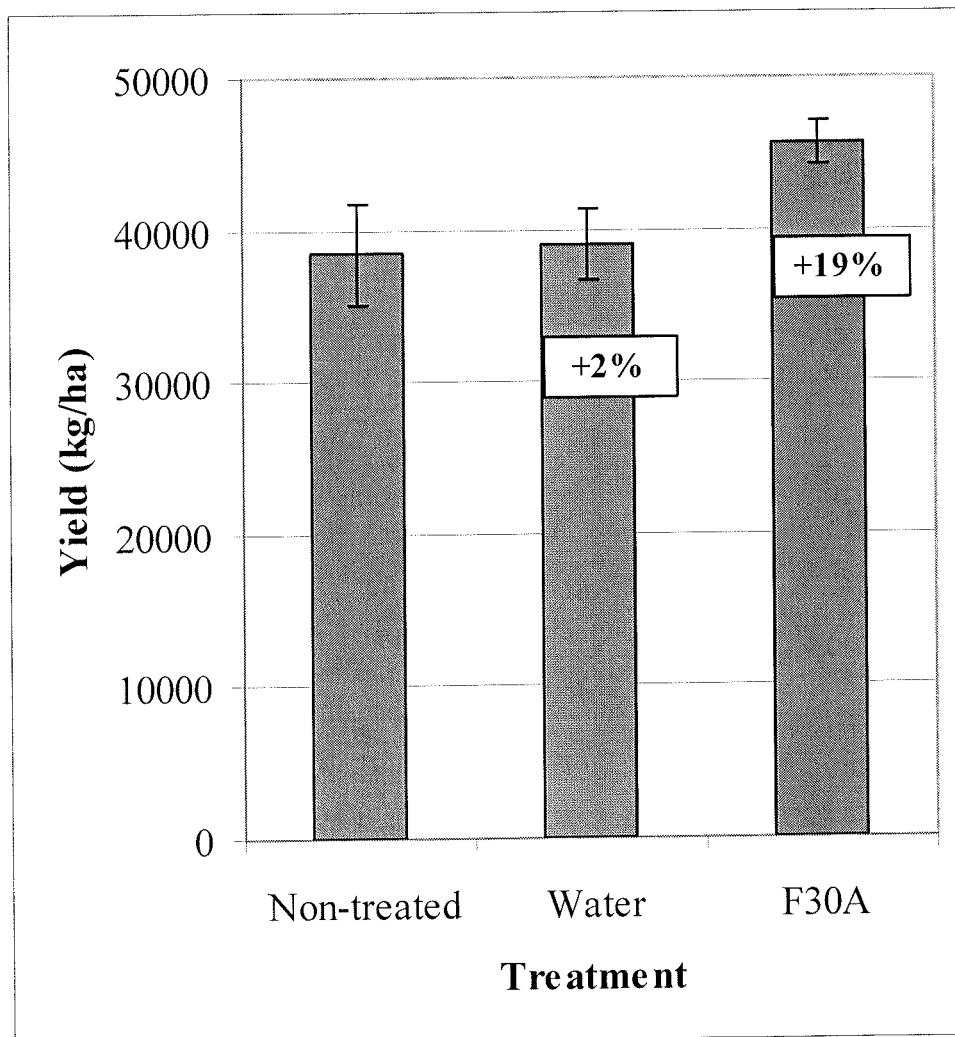
FIG. 13. Carrot yield after seed application with the F30A fermentation product (batch FOM076) in field experiment. Error bars represent standard error of the mean (non-treated: n=9; water: n=12; F30A: n=6).

The same principles as for field trials with seed treatment of other crops were used in experiments with carrot. Field trials were placed in Southern Sweden at commercial farms growing carrot; 300 or 100 ml of the fermentation products were usually applied per kilogram seeds and plot area differed from 20 to 30 m² depending on the trial. Yield was measured after randomly harvesting carrots from 0.5 or 1-meter row (n=3) from each treatment. The carrots from each treatment and repetition were collected, counted and weighed separately. An exemplary field trial demonstrating improvement of carrot yield was performed in Southern Sweden. In this field trial carrot seeds were treated with a dosage of 300 ml/kg of the fermentation product of the isolate of invention (batch FOM076, fermented according to the standard protocol); controls were non-treated seeds and seeds treated with water. FIG. 13 shows the data on the yield increase (around 19% when compared to controls) after application of the isolate of invention.

Example 12

Enhancement of Yield—an Example from the Field Trials with Root/Soil Treatment of Iceberg Lettuce In field trials with root/soil treatment of iceberg lettuce, commercially grown plantlets were each treated with 10 ml of the fermentation product of the isolate of invention, fermented according to the standard or to the optimized protocol. Treatment was usually done during the plantlet transplantation to the field. Prior to the treatment the fermentation product(s) were usually diluted in proportions 1 part of fermentation product ($5.0 \times 10^9$ to $1.0 \times 10^{10}$ cfu per ml, depending on the batch of the fermentation product) and 1 part of tap water. Optionally, plantlets may also be treated with the various preparations of the bacterial cells of the isolate of invention re-hydrated in appropriate inorganic or organic agriculturally compatible solvents. Prior to transplantation trays with plantlets (150 to 300 plants per each treatment) were drenched in appropriate volume of the fermentation product, or the same volume of water as control, and then transplanted to the field. If needed plantlets may be also treated a few days prior to transplantation and stored according to commercial agricultural practices. Standards used for iceberg lettuce field cultivation (30 cm space between rows and 27 cm space between plants) were followed during transplantation. Lettuce was harvested according to common agricultural practices and yield increase was measured in gram of weight increase per each iceberg head.

Figure 14:
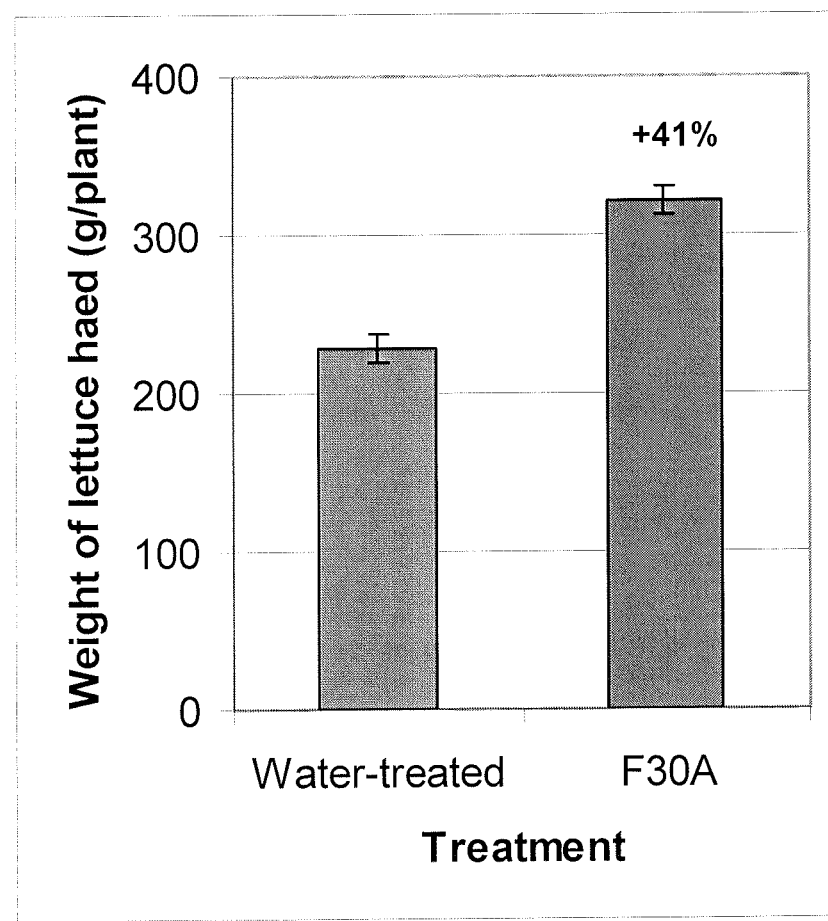
FIG. 14. Iceberg lettuce yield after root/soil application with the F30A fermentation product (batch FOM233) in field experiment. Error bars represent standard error of the mean (n=5).

FIG. 14 shows the data from the field experiment performed in Southern Sweden. In this trial the yield of iceberg lettuce (g per one lettuce head) was increased by on average 41% as compared to the average yield of obtained from water-treated plants.

Example 13

Figure 15:
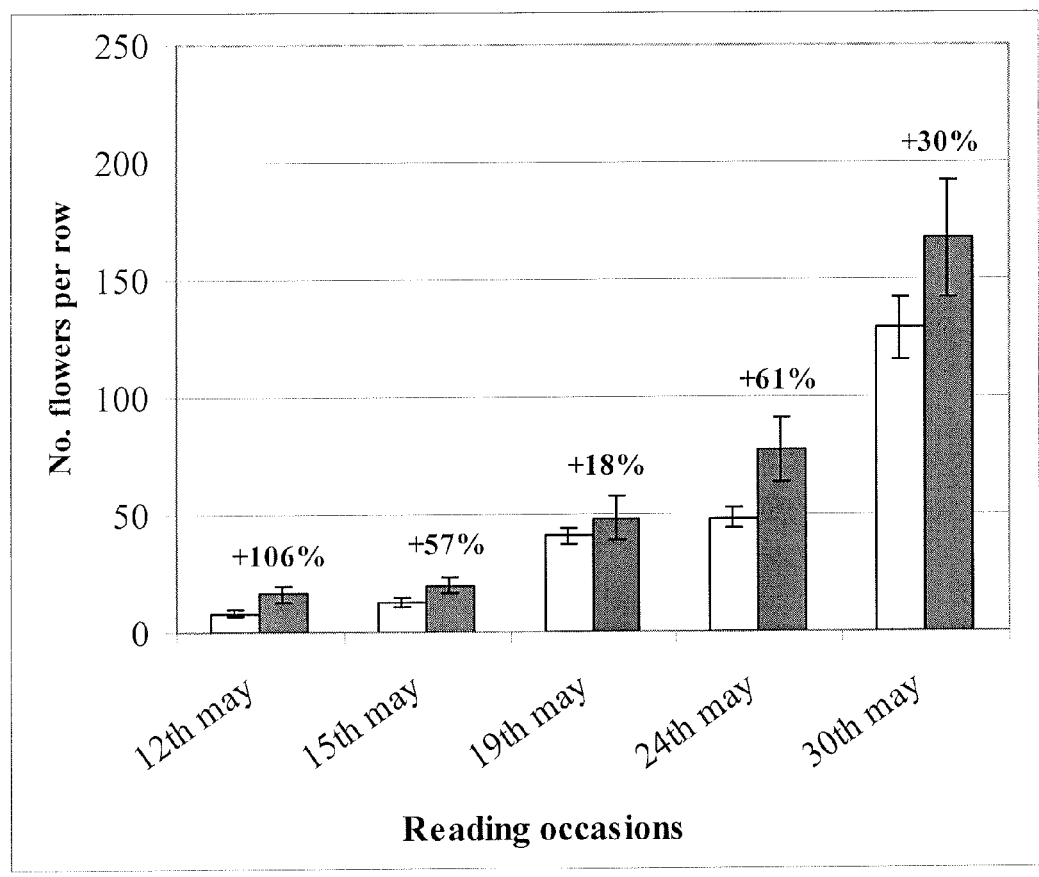
FIG. 15. Number of strawberry flowers after root/soil application with the F30A fermentation product (batches FOM095 and FOM147) in field experiment. Dark bars: F30A; light bars: water-treated control. Error bars represent standard error of the mean (n=4).
Figure 16:
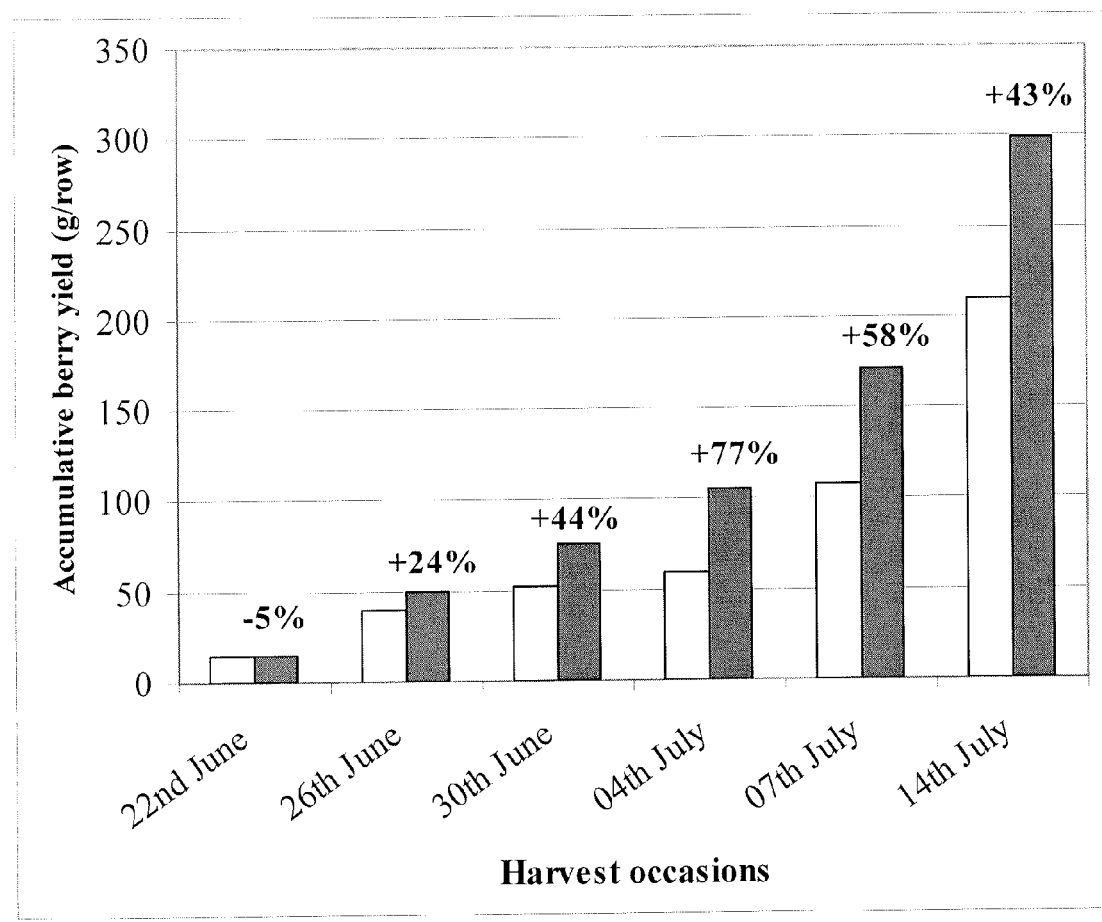
FIG. 16. Yield of strawberries after root/soil application with the F30A fermentation product (batches FOM095 and FOM147) in field experiment. Dark bars: F30A; light bars: water-treated control. Error bars represent standard error of the mean (n=4).

Enhancement of Flowering and Yield—an Example from the Field Trials with Root/Soil Treatment of Strawberry In field trials with root/soil treatment of strawberry, commercially grown plantlets were each treated with 10 ml of the fermentation product of the isolate of invention (batch FOM095, fermented according to standard protocol, around $1.2 \times 10^{10}$ cfu per ml) at the plantlets transplantation to the field during the summer. This was followed by the second treatment performed as plant watering during the following spring with 20 ml of the fermentation product (batch FOM147, fermented according to optimized protocol, around $3.1 \times 10^9$ cfu per ml). If necessary, adjustments to appropriate concentrations of the fermentation products were done by dilution with tap water. For both treatments, application of the same volume of water was used as control. Commercial plantlets were used in the trial, which were planted according to standards used for strawberry field cultivation (90 cm space between rows and 30 cm space between plants). Measurements of the number of established flowers were done at 7 separate occasions and ripened strawberries were harvested at 6 separate occasions for the yield measurement. FIGS. 15 and 16 show the improvement of flower establishment and the improvement of the yield of berries detected during the second growing season. Both the improvement of flowering and the yield improvement are apparent during all reading occasions with exception of the first harvest of the berries, and significant over the whole blooming and harvest season. Depending on the reading occasion the blooming was improved from 20% (reading on $30^{th}$ of May) up to 142% (reading on $12^{th}$ of May), which is shown in FIG. 15.

Improvement of blooming resulted also in a significant increase of the yield of berries. The accumulative yield over the whole harvest season was totally higher by 43% when compared to the yield of berries obtained from water-treated control plants (FIG. 16).

Example 14

Figure 17:
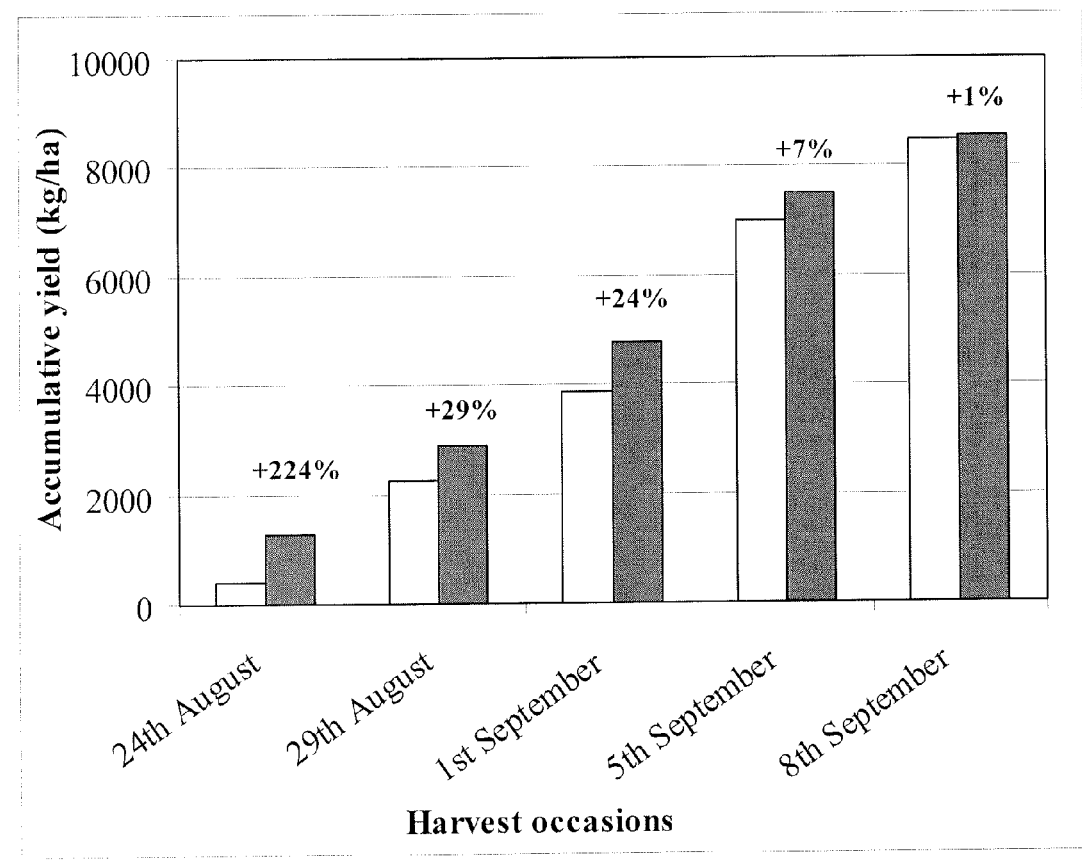
FIG. 17. Yield of broccoli after root/soil application with the F30A fermentation product (batch FOM076) in field experiment. Dark bars: F30A; light bars: water-treated control. Error bars represent standard error of the mean (n=5).

Improvement of the Maturity of Broccoli and its Early Yield—an Example from the Field Trials with Root/Soil Treatment of Broccoli In field trials with root/soil treatment of broccoli, commercially grown plantlets were treated with 10 ml per plantlet of the fermentation product of the isolate of invention, fermented according to the standard or to the optimized protocol. Treatment was usually done during the plantlet transplantation to the field. Prior to the treatment the fermentation product(s) were diluted with tap water in order to adjust cell concentration to around $2.5$-$7.5 \times 10^9$ cfu per ml. Prior to transplantation trays with plantlets were drenched in appropriate volume of the fermentation product, or the same volume of water as control, and then transplanted to the field. If needed plantlets can also be treated a few days prior to transplantation and stored according to commercial agricultural practices. Standards used for broccoli field cultivation (30 cm space between rows and 30 cm space between plants or 50 cm space between rows and 50 cm space between plants) were followed during transplantation. Broccoli is harvested according to common agricultural practices at several occasions. Yield increase was at first recorded in gram per plot; plots of 20 m$^2$ are usually used, and then re-calculated into corresponding yield in kilogram per hectare. FIG. 17 shows the data on accumulative yield of broccoli harvested at five separate occasions during the field experiment performed in Southern Sweden; with the fermentation product batch FOM076 (fermented according to the standard protocol, around $6.5 \times 10^9$ cfu per ml). The effect of the application of the isolate of invention was stunning especially during the beginning of the harvesting period. The amount of mature and ready to harvest broccoli was improved by over 200% during the first harvest and over 20% during the second and the third harvests when compared to the yield obtained from water-treated control plantlets (FIG. 17). Although the improvement of the harvest was not as strong at the end of the harvesting season, economically the improved early maturity is of exceptional importance for the potential users/farmer as on average plants treated with the isolate of invention could have been harvested 5 days earlier when compared to those water-treated.

Example 15

Figure 18:
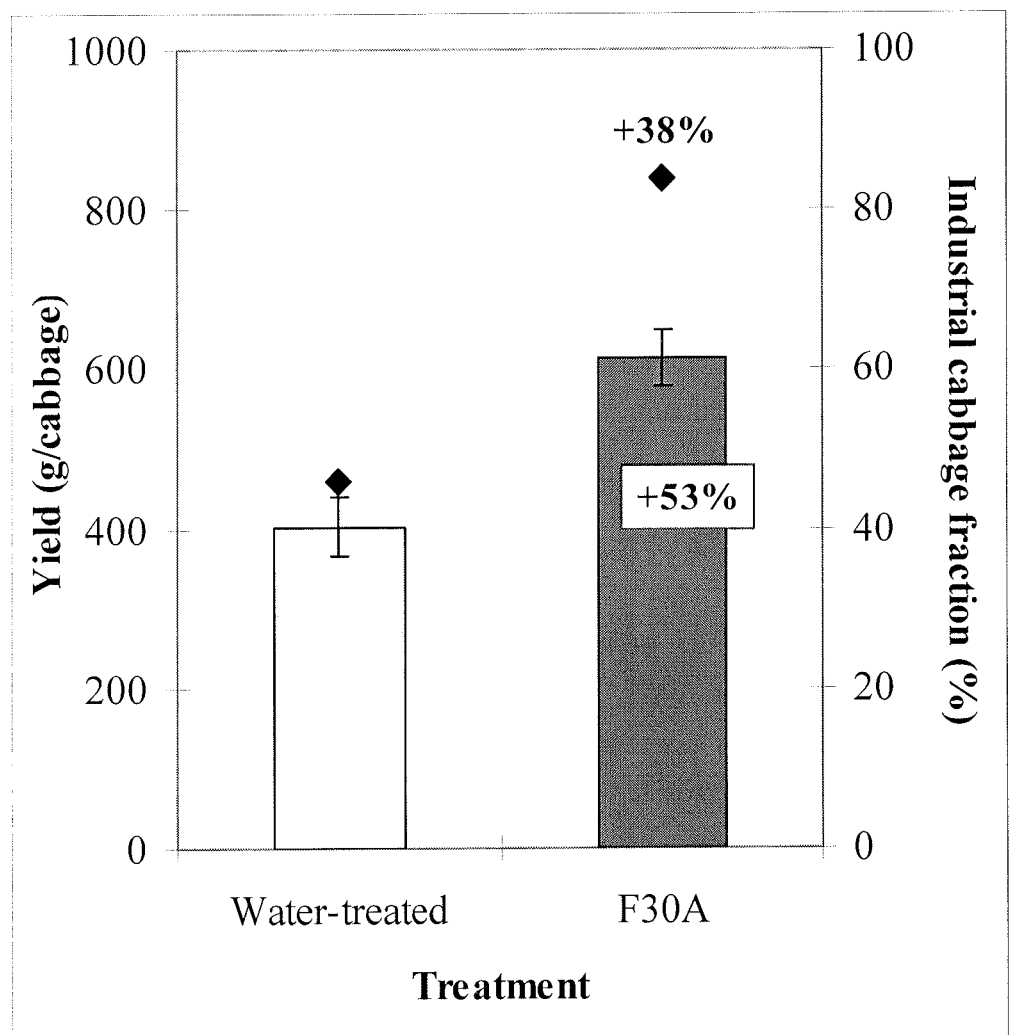
FIG. 18. Yield of summer cabbage after root/soil application with the F30A fermentation product in field experiment. Dark bars: F30A; light bars: water-treated control; squares: percentage marketable yield (>350 gram). Error bars represent standard error of the mean (n=50).

Enhancement of Yield and Improvement of the Cabbage Quality—an Example from the Field Trials with Root/Soil Treatment of Cabbage In field trials with root/soil treatment of cabbage, commercially grown plantlets were treated with between 5 and 10 ml per plantlet of the fermentation product of the isolate of invention fermented according to the standard or to the optimized protocol and treatment was usually done during the plantlet transplantation to the field. Prior to the treatment the fermentation product(s) were diluted with tap water in order to adjust cell concentration to around $5.0$-$7.0 \times 10^9$ cfu per ml. Prior to transplantation trays with plantlets were drenched in appropriate volume of the fermentation product, or the same volume of water as control, and then transplanted to the field. If needed plantlets can be treated a few days prior to transplantation and stored according to commercial agricultural practices. Standards used for cabbage field cultivation (50 cm space between rows and 50 cm space between plants) were followed during transplantation. Cabbage was harvested according to common agricultural practices and the weight of each cabbage head was estimated. FIG. 18 shows the data on improvement of yield in early summer cabbage (large scale trial; 50 cabbage plantlets per treatment, 5 blocks) after the treatment with the fermentation product batch FOM154 (5 ml, fermented according to the optimized protocol, around $6.5 \times 10^9$ cfu per ml). In this trial the weight of cabbage heads were increased by 53% (FIG. 18) after the application of the isolate of invention.

Moreover the increase of the yield, the significant improvement of the cabbage marketable fraction (approved for selling) was also detected (FIG. 18; +38% as compared to water-treated plantlets). This is of significant economical importance for potential users/farmers.

Example 16

Enhancement of Yield and Improvement of the Tuber Quality—en Example from the Field Trials with Potato Tuber Treatment The potato field experiments with the exception of one large-scale trial were set up in a randomised block design with 5 repetitions. Every repetition of each treatment included 60 seed tuber that were sown in two or three rows. The row and seed distances were followed according to the conventional practices in potato farming. The potato trials were located in Skåne and in Uppland/Dalarna (middle part of Sweden). Trials were performed both in new and late potato cultivars. In the new potato, the whole field trials were covered after planting until the plants were fully developed, according to normal cultivation practice. In one of the first new potato field experiments, an uncovered treatment was included. Potato tubers were treated in direct connection to planting or up to ten days in advance. In general, the fermentation product fermented according to the standard or to the optimized protocol was diluted to 50% strength using ordinary tap water for the treatment of tubers, but the effect of 10% strength fermentation product was also evaluated. The tubers were dipped in respective bacterial preparations for 20-30 minutes, and then they were planted with a commercial potato-planting machine. In the case treatments were performed several days prior to planting, the inoculated tubers were air-dried before being placed in the potato storage. By dipping, each potato tuber received around 0.75 to 1 ml of bacterial suspension. In addition, another method of bacterial application was performed using a standard spraying device that is commercially used for chemical treatment of potato tubers. Using this device tubers were sprayed at the dosage of 4 liter bacterial suspension per ton, meaning that each tuber received approximately 0.2 ml of suspension. The efficacy of this inoculation method was also evaluated by spraying tubers at different time points, from one to three months prior to planting. To improve attachment and enhance protection of bacteria on potato seed tubers a wet formulation including a combination of an agriculturally compatible sticker compound and a surfactant, both with good environmental profiles, was developed. This formulation was applied in field experiments, both in dipping and spraying treatments. Emergence/plant establishment, time of flowering, eventual disease symptoms and yield/marketable yield were scored and measured in all field trials.

Figure 19:
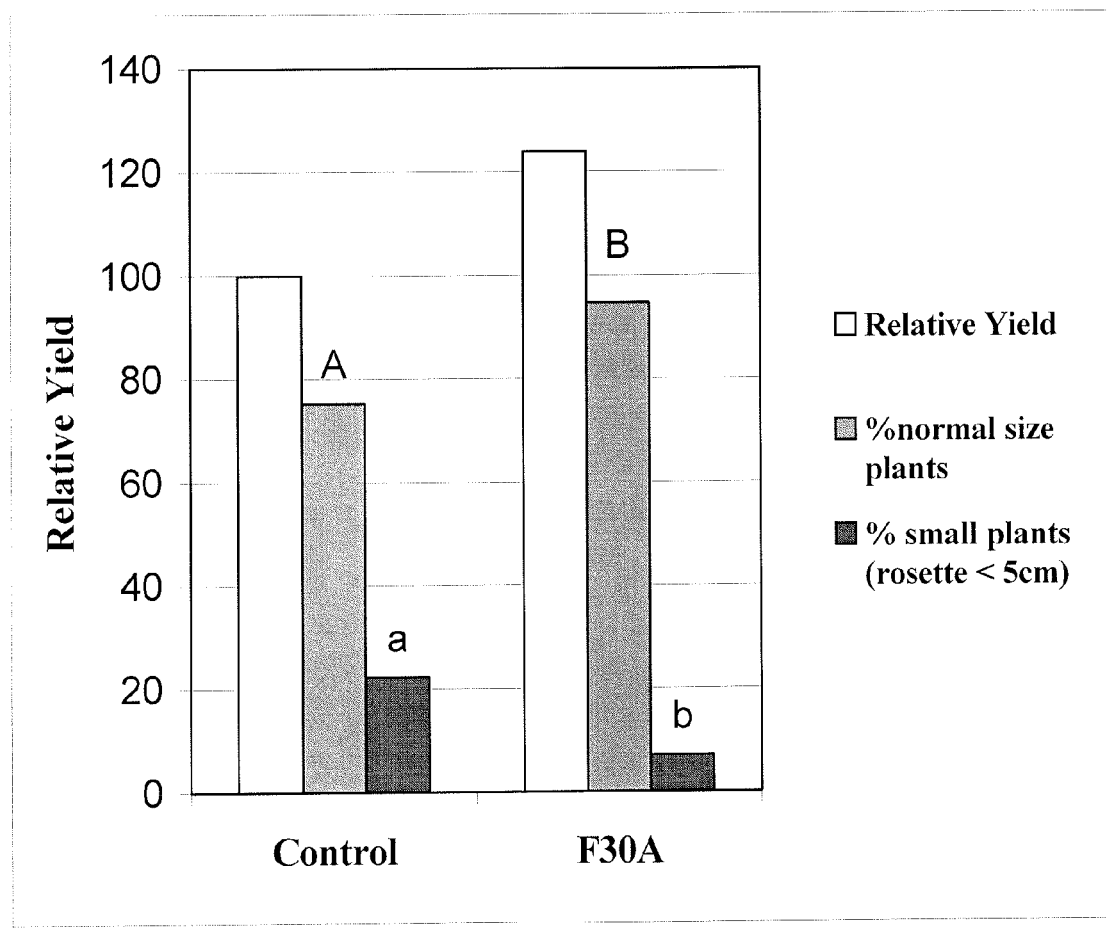
FIG. 19. Plant development and tuber yield of new potato after tuber application with the F30A fermentation product in field experiment. Means with different letters are significantly different, according to Duncan's multiple range test (p=0.05).

The effect of the isolate of invention in the new potato cultivar 'Rocket' is shown in FIG. 19. The bacterial treatment significantly improved the development of emerged plants and increased the final yield, with an average yield increase of 24%.

Figure 20:
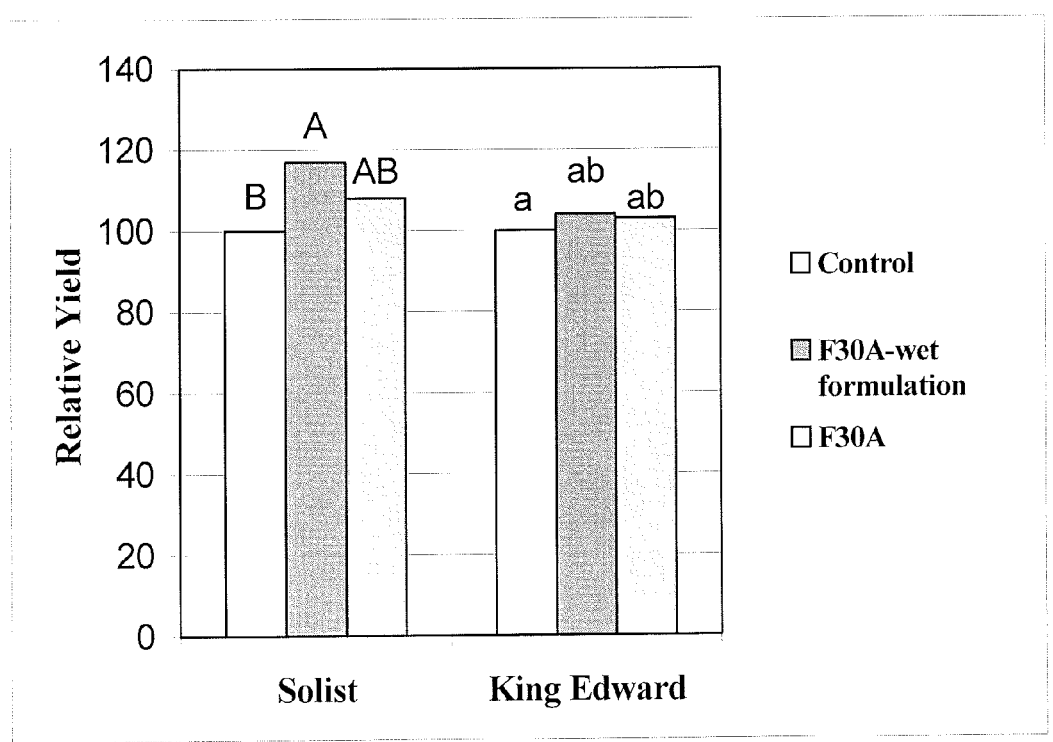
FIG. 20. Relative tuber yield in one new potato and one late potato cultivar, after tuber application with the F30A fermentation product and with a wet formulation of the isolate. Data from field experiments. Means with different letters are significantly different, according to Duncan's multiple range test (p=0.05).

The application of the wet formulation of the isolate of invention in the early and late potato cultivars improved the final tuber yield with 17% (new potato) and with 4% (late potato), as compared to corresponding yield increases of 8% and 3% after application of the non-formulated fermentation product (FIG. 20).

Example 17

Enhancement of Root and Plant Growth of Trees in Plant Nurseries

Figure 21:
FIG. 21. Enhancement of the root and the shoot growth of 10-weeks old plantlets of Scots pine, after treatment with the fermentation product of the isolate F30A (to the right) in comparison to the non-treated plantlet (to the left).

In order to test effects of the application of the isolate of invention on growth improvement of tree plantlets in plant nurseries, the fermentation product of the isolate of invention, cultured according to the optimized fermentation protocol, was used to treat newly emerged plantlets of Scots pine. The seeds were sown and treated according to commercial practices and methods used in plant nurseries. Plantlets were watered with 5 ml of the fermentation product ($2$-$3.5 \times 10^9$ per ml) per plantlet 9 days after sowing; controls were plantlets treated with the same amount of water. The growth of plantlets was visually monitored 3, 6 and 10 weeks after the treatments. Thirteen weeks after the treatments dry weight of the roots and shoots were measured after collecting representative samples of the plantlets. The results summarized in Table 5 show that the application of the isolate of invention results in higher dry weight of roots and shoots of Scots pine plantlets, which is also illustrated in FIG. 21. The dry weight of root is up to 14% and dry weight of upper plant up to 31% higher when compared to water treated control. The total weight of plantlets treated with the isolate of invention is thus up to 25% higher than the weight of water treated control plantlets. The *Pseudomonas azotoformans*, strain F30A, of the present invention may therefore also be used for improving the growth of trees and/or tree plantlets.

TABLE 5

Improvement of dry weight of Scots pine plantlets after application of the isolate of invention.

| Treatment | No. collected plantlets | Mean weight per plantlet (g)/percentage improvement (%) | | | | | |
|---|---|---|---|---|---|---|---|
| | | Root | | Upper plant | | Total | |
| Water | 29 | 0.21 g | | 0.39 g | | 0.60 g | |
| Fermentation product ($2.0 \times 10^9$ per ml) | 27 | 0.24 g | 14% | 0.51 g | 31% | 0.75 g | 25% |
| Fermentation product ($3.3 \times 10^9$ per ml) | 30 | 0.22 g | 5% | 0.49 g | 26% | 0.71 g | 18% |

Example 18

Compatibility with agricultural products. Examples from growth of the isolate of invention together with active ingredients from biological, organic and chemical agricultural products.

TABLE 6

Compatibility limit values (µg ml$^{-1}$), based on respective recommended dosages for seed treatment, for selected synthetic chemical fungicides and organic ingredients commercially used for seed-treatment and compatibility values (µg ml$^{-1}$) at which growth of *P. azotoformans* F30A ($3.3 \times 10^8$ ml$^{-1}$) is not inhibited in the presence of tested compounds.

| Active ingredient | Ingredient compatibility limit value (µg/ml) | Compatibility value (µg/ml) of the combination ingredient/*P. azotoformans* F30A ($3.3 \times 10^8$ ml$^{-1}$) |
|---|---|---|
| Metalaxyl-M | 710 | >1000 |
| Iprodion | 1930 | >1000* |
| Thiram | 3200 | >3520 |
| Chitosan | 360 | >1000 |
| Humic and fulvic acids | 25 | >1000 |

*)Higher concentrations could not be tested due to precipitation.

TABLE 7

Compatibility of the *P. azotoformans* F30A with three commercial biocontrol agents according to the junction assay (dual plate assay).

| Bacterial isolate A | Bacterial isolate B | Compatibility |
|---|---|---|
| *P. azotoformans* F30 A | *Pseudomonas* sp. | Full (+++) |
| *P. azotoformans* F30 A | *Bacillus* sp. A | Full (+++) |
| *P. azotoformans* F30 A | *Bacillus* sp. B | Full (+++) |

In all the examples above the isolate of invention did not show any sign of impaired growth and was hence fully compatible with all the commercially available active ingredients at concentrations recommended for seed treatment.

REFERENCES

1. Benizri, E., Baudoin, E. Guckert, A. 2001: Root Colonization by Inoculated Plant Growth-Promoting Rhizobacteria. Biocontrol Science and Technology 11: 557-574Brisbane, P. G., Harris, J. R., and Moen, R. 1989: Inhibition of fungi from wheat roots by *Pseudomonas fluorescens* 2-79. Soil Biol. Biochem. 21: 1019-1026.
2. Compant, S., Duffy, B, Nowak, J., Clement, C. and d Ait Barka, E. 2005. Use of Plant Growth-Promoting Bacteria for Biocontrol of Plant Diseases: Principles, Mechanisms of Action, and Future Prospects. Appl. and Environ. Microbiol., September 2005, p. 4951-4959 Vol. 71, No. 9
3. Dabboussi, F., Hamze, M., Elomari, M., Verhille, S., Baida, N., Izard, D. and Leclerc, H. 1999: *Pseudomonas libanensis* sp. nov., a new species isolated from Lebanese spring waters. Int J Syst Bacteriol. 49: 1091-1101.
4. Davies, K. G., and Whitbread, R. 1989: Factors affecting the colonisation of a root system by fluorescent Pseudomonads: The effects of water, temperature and soil microflora. Plant and Soil 116: 247-256.
5. Deshwal, V. K., Kumar, T., Dubey, R. C. and Maheshwari, D. K., 2006: Long-term effect of *Pseudomonas aeruginosa* GRC1 on yield of subsequent crops of paddy after mustard seed bacterization. Current Science 91: 423-424.
6. DeFreitas, R. J. and Germida, J. J. 1991: *Pseudomonas cepacia* and *Pseudomonas putida* as winter wheat inoculants for biocontrol of *Rhizoctonia solani*. Canadian journal of microbiology 37: 780-784.
7. Dowling, D. N. and F. O'. Gara. 1994: Metabolites of *Pseudomonas* involved in the biocontrol of plant disease. Trends Biotechnol. 12: 133-141.
8. García de Salamone, I. E., Hynes, R. K. and Nelson, L. M. 2001: Cytokinin production by plant growth promoting rhizobacteria and selected mutants. Can. J. Microbial. 47: 404-411.
9. Gerhardson, B., Alström, S. and Ramert, B. 1985: Plant reactions to inoculation of roots with fungi and bacteria. Phytopathol. Z. 114: 108-117.
10. Hemming B C. 1990: Bacteria as antagonists in biological control of plant pathogens. In: Baker R R, Dunn P E, eds. New directions in biological control: Alternatives for suppressing agricultural pests and diseases. New York: Alan R. Liss. 223-242.
11. Hökeberg, M., Gerhardson, B. amd Johnsson, L. 1997. Biological control of cereal seed-borne diseases by seed bacterization with greenhouse selected bacteria. Europea Journal of Plant Pathology 103, 25-33.

12. Howie W J. and Echandi E (1983) Rhizobacteria: Influence of cultivar and soil type on plant growth and yield of potato. Science 4:86.
13. Kloepper, J. W., Leong, J., Teintze, M., and Schroth, M. N. 1980a: Enhanced plant growth by siderophores produced by plant growth promoting rhizobacteria. Nature 286:885-886
14. Kloepper J W, Scrhoth M N, Miller T D 1980b: Effects of rhizosphere colonization by plant growth-promoting rhizobacteria on potato plant development and yield Phytopathology 70: 1078-1082.
15. Kloepper, J W and Schroth, M N. 1978. Plant growth promoting rhizobacteria on radishes. Proc. 4th Int. Conference on Plant Pathogenic bacteria. Angrs 879-882.
16. Kropp B R, Thomas E, Pounder J I, Anderson A J. 1996: Increased emergence of spring wheat after inoculation with *Pseudomonas chlororaphis* isolate 2E3 under field and laboratory conditions. Biology and fertility of soils. 23: 200-206.
17. Levenfors, J. P., Eberhard T. H., Levenfors, J. J., Gerhardson B. and Hökeberg M. 2008: Biological control of snow mould (*Microdochium nivale*) in winter cereals by *Pseudomonas brassicacearum*, MA250. BioControl 53: 651-665.
18. Micsinai, A., Borsodi, A. K., Csengeri, V., Horvath, A., Oravecz, O., Nikolausz, M., Reskone, M. N. and Marialigeti, K. 2003 Rhizome-associated bacterial communities of healthy and declining reed stands in Lake Velencei, Hungary. Hydrobiologia 506: 707-713.
19. Maeng, J. and Khudairi, A. K. 1973: Studies on the flowering mechanism in Lemna. I. Amino acids changes during flower induction. Physiol. Plant 28: 264-270.
20. Loper, J. E. and Buyer, J. S., 1991. Siderophores in microbial interactions on plant surfaces. Molecular Plant-Microbe Interactions 4: 5-13.
21. Lucy, M., Reed, E., and Glick, B. R. 2004 Applications of free living plant growth-promoting rhizobacteria. Antonie van Leeuwenhoek 86: 1-25.
22. Lugtenberg, B. and Kamilova, F. 2009. Plant-Growth-Promoting Rhizobacteria Annual Review of Microbiology Vol. 63: 541-556
22. Patten, C. and Glick, B. R. 1996: Bacterial biosynthesis of indole-3-acetic acid. Can. J. Microbiol. 42:207-220.
23. Piao, Z., Cui, Z., Yin, B., Hu, J., Zhou, C., Xie, G., Su, B. and Yin, S. 2005: Changes in acetylene reduction activities and effects of inoculated rhizosphere nitrogen-fixing bacteria on rice. Biology and Fertility of Soils 41: 371-378.
24. Stanier, R. Y., Palleroni, N. J. and Doudoroff, M. 1966: The aerobic pseudomonads: a taxonomic study. Journal of General Microbiology 43: 159-271.
25. Suslow, T. V. and Schroth, M. N. 1982: Rhizobacteria of sugar beets: Effects of seed application and root colonization on yield. Phytopathology 72:199-206.
26. O'Sullivan, D. J. and O'Gara F. 1992: Traits of fluorescent *Pseudomonas* spp. involved in suppression of plant root pathogens. Microbiol Mol Biol Rev. 56: 662-676.
27. Urashima, Y., Suga, Y. and Hori, K. 2006: Growth Promotion of Spinach by Fluorescent *Pseudomonas* Strains under Application of Organic Materials. Soil Science & Plant Nutrition 51: 841-847.
28. Vivekananthan, R., Ravia, M., Saravanakumara, D., Kumarb, N., Prakasama V. and Samiyappana, R. 2004: Microbially induced defense related proteins against post-harvest anthracnose infection in mango. Crop Protection 23:11, 1061-1067
29. Weller, D. M. 1988: Biological Control of Soilborne Plant Pathogens in the Rhizosphere with Bacteria. Annual Review of Phytopathology 26: 379-407.
30. Kloepper, J. W., Scher, W. and Murphy, F. 1986: Emergence-promoting rhizobacteria PCT/US1986/001375, WO/1987/000194
31. Kloepper, J. W. and Scher, F. 1996 Plant growth-promoting rhizobacteria for agronomic, nonroot crops US1996/5503651
32. Kloepper, J. W., Simonson, C. and Lifshitz, R. 1996: Bacterial cultures for root-colonizing plants. US1996/5503652
33. Nautiyal C. S. 2002: Biologically pure culture of bacteria, which suppresses diseases caused by pathogens in chickpea crops and a culture of bacteria comprising a strain of *Pseudomonas fluorescens*. US2002/6495362
34. Raaijmakers, J. M., Weller, D. M., Tomashow, L. S, and Cook, R. J. 2002: Biocontrol agents for take-all. US2002/6447770
35. Tuzun, S., Kloepper, J. W., Rodrigues-Kabana, R., and Kenney, D. S. Biological compositions and methods for enhancing plant growth and health and producing disease-suppressive plants 2000: PCT/US2000/005147, WO00051435

The invention claimed is:

1. A biologically pure strain of *Pseudomonas azotoformans*, strain F30A, which has been deposited at Deutsche Sammlung von Mikroorganismen und Zellkulturen GmbH and has been assigned accession number DSM 22077.

2. A supernatant obtained from a culture of a biologically pure strain of *Pseudomonas azotoformans*, strain F30A, which has been deposited at Deutsche Sammlung von Mikroorganismen und Zellkulturen GmbH and has been assigned accession number DSM 22077.

3. A method for enhancing seed germination, plant emergence, plant growth, or a combination thereof, wherein said method comprises contacting a seed or a plant with a biologically pure strain of *Pseudomonas azotoformans*, strain F30A, which has been deposited at Deutsche Sammlung von Mikroorganismen und Zellkulturen GmbH and has been assigned accession number DSM 22077 or a supernatant obtained from a culture of said biologically pure strain.

4. The method of claim 3, wherein said seed is dicotyledonous, and said plant is dicotyledonous.

5. The method of claim 3, wherein said seed is monocotyledonous, and said plant is monocotyledonous.

6. A fermentation product of a biologically pure strain of *Pseudomonas azotoformans*, strain F30A, which has been deposited at Deutsche Sammlung von Mikroorganismen und Zellkulturen GmbH and has been assigned accession number DSM 22077, said fermentation product comprising *Pseudomonas azotoformans* strain F30A bacterial cells obtained from the biologically pure strain and their used growth medium.

7. An agricultural composition comprising a biologically pure strain of *Pseudomonas azotoformans*, strain F30A, which has been deposited at Deutsche Sammlung von Mikroorganismen und Zellkulturen GmbH and has been assigned accession number DSM 22077 or a supernatant obtained from a culture of said biologically pure strain.

8. The agricultural composition of claim 7, wherein said composition comprises one or more agents selected from the group consisting of additional plant growth promoting microorganisms, bio-control microorganisms, organic fertilizers, and agrochemicals.

9. A method for enhancing seed germination, plant emergence, plant growth, or a combination thereof, wherein said method comprises applying a fermentation product or an agricultural composition to a seed, a plant, or an environment surrounding said seed or said plant, wherein said fermentation product is a fermentation product of a biologically pure strain of *Pseudomonas azotoformans*, strain F30A, which has been deposited at Deutsche Sammlung von Mikroorganismen und Zellkulturen GmbH and has been assigned accession number DSM 22077, and wherein said agricultural composition is an agricultural composition comprising said biologically pure strain or a supernatant obtained from a culture of said biologically pure strain.

10. The method of claim 9, wherein said fermentation product or said agricultural composition is applied to roots of said plant.

11. The method of claim 9, wherein said fermentation product or said agricultural composition is applied to soil before or after emergence of plant roots.

12. The method of claim 9, wherein said fermentation product or said agricultural composition is applied to plant vegetative propagation units.

13. The method of claim 9, wherein said fermentation product or said agricultural composition is applied to plant growing media surrounding said seeds or said plants.

14. The method of claim 9, wherein said plant is, and said seed will develop into, a monocotyledonous plant.

15. The method of claim 9, wherein said plant is, and said seed will develop into, a dicotyledonous plant.

16. A method for preparing an agricultural composition, wherein said method comprises mixing *Pseudomonas azotoformans*, strain F30A, which has been deposited at Deutsche Sammlung von Mikroorganismen and Zellkulturen GmbH and has been assigned accession number DSM 22077, or a supernatant obtained from a culture of said strain with one or more liquid or solid carriers to form said agricultural composition.

17. The method of claim 16, wherein said method comprises mixing one or more agents selected from the group consisting of additional plant growth promoting microorganisms, bio-control microorganisms, organic fertilizers, and agrochemicals with said strain or said supernatant.

18. The agricultural composition of claim 7, wherein said composition comprises one or more liquid carriers.

19. The agricultural composition of claim 7, wherein said composition comprises one or more solid carriers.

* * * * *

UNITED STATES PATENT AND TRADEMARK OFFICE
CERTIFICATE OF CORRECTION

PATENT NO. : 8,796,179 B2  
APPLICATION NO. : 13/514929  
DATED : August 5, 2014  
INVENTOR(S) : Jolanta Levenfors et al.

Page 1 of 1

It is certified that error appears in the above-identified patent and that said Letters Patent is hereby corrected as shown below:

In the Claims

Column 30, line 8 (claim 16), delete "and" and insert -- und --, therefor.

Signed and Sealed this
Seventeenth Day of March, 2015

Michelle K. Lee
*Director of the United States Patent and Trademark Office*